(12) United States Patent
Ryder et al.

(10) Patent No.: US 11,444,595 B2
(45) Date of Patent: Sep. 13, 2022

(54) ACOUSTIC RESONATOR DEVICE WITH CONTROLLED PLACEMENT OF FUNCTIONALIZATION MATERIAL

(71) Applicant: Qorvo Biotechnologies, LLC, Plymouth, MN (US)

(72) Inventors: Matthew Ryder, Bend, OR (US); Rio Rivas, Bend, OR (US); Thayne Edwards, Bend, OR (US)

(73) Assignee: Qorvo Biotechnologies, LLC, Plymouth, MN (US)

( * ) Notice: Subject to any disclaimer, the term of this patent is extended or adjusted under 35 U.S.C. 154(b) by 1244 days.

(21) Appl. No.: 15/334,459

(22) Filed: Oct. 26, 2016

(65) Prior Publication Data

US 2018/0048280 A1      Feb. 15, 2018

Related U.S. Application Data

(60) Provisional application No. 62/373,668, filed on Aug. 11, 2016.

(51) Int. Cl.
*H03B 5/30*     (2006.01)
*H03H 9/02*     (2006.01)
(Continued)

(52) U.S. Cl.
CPC ....... *H03H 9/02015* (2013.01); *G01N 29/022* (2013.01); *G01N 29/036* (2013.01);
(Continued)

(58) Field of Classification Search
CPC .... H03H 9/02015; H03H 9/175; H03H 9/131; H03H 3/02; H03H 2003/027;
(Continued)

(56) References Cited

U.S. PATENT DOCUMENTS 4,640,756 A   2/1987  Wang et al.
5,910,286 A   6/1999  Lipskier
(Continued)

FOREIGN PATENT DOCUMENTS

CN   1894583 A   1/2007
CN   103472129 A   12/2013
(Continued)

OTHER PUBLICATIONS

U.S. Appl. No. 15/293,063, filed Oct. 13, 2016, McCarron et al.
(Continued)

*Primary Examiner* — Richard Tan
(74) *Attorney, Agent, or Firm* — Haynes Boone, LLP; Benjamin C. Pelletier; Destiny L. Stephenson

(57) ABSTRACT

A micro-electrical-mechanical system (MEMS) resonator device includes at least one functionalization material arranged over at least a central portion, but less than an entirety, of a top side electrode. For an active region exhibiting greatest sensitivity at a center point and reduced sensitivity along its periphery, omitting functionalization material over at least one peripheral portion of a resonator active region prevents analyte binding in regions of lowest sensitivity. The at least one functionalization material extends a maximum length in a range of from about 20% to about 95% of an active area length and extends a maximum width in a range of from about 50% to 100% of an active area width. Methods for fabricating MEMS resonator devices are also provided.

21 Claims, 13 Drawing Sheets

(51) Int. Cl.

| | |
|---|---|
| *G01N 29/02* | (2006.01) |
| *G01N 29/036* | (2006.01) |
| *G01N 33/536* | (2006.01) |
| *H03H 3/02* | (2006.01) |
| *H03H 9/13* | (2006.01) |
| *H03H 9/17* | (2006.01) |
| *H03H 9/15* | (2006.01) |

(52) U.S. Cl.
CPC ............ *G01N 33/536* (2013.01); *H03H 3/02* (2013.01); *H03H 9/131* (2013.01); *H03H 9/175* (2013.01); *G01N 2291/0255* (2013.01); *G01N 2291/0256* (2013.01); *G01N 2291/0426* (2013.01); *H03H 2003/027* (2013.01); *H03H 2009/155* (2013.01)

(58) Field of Classification Search
CPC ........... H03H 2009/155; G01N 29/036; G01N 29/022; G01N 33/536; G01N 2291/0426; G01N 2291/0256; G01N 2291/0255
USPC ........................................................ 331/154
See application file for complete search history.

(56) References Cited

U.S. PATENT DOCUMENTS

| | | | |
|---|---|---|---|
| 6,320,295 | B1 | 11/2001 | McGill et al. |
| 7,468,608 | B2 | 12/2008 | Feucht et al. |
| 8,409,875 | B2 | 4/2013 | Johal et al. |
| 8,448,494 | B2* | 5/2013 | Mastromatteo .......... G01G 3/13 73/23.34 |
| 2005/0148065 | A1* | 7/2005 | Zhang .................... B82Y 15/00 435/287.2 |
| 2006/0125489 | A1* | 6/2006 | Feucht ................. G01N 29/022 324/633 |
| 2007/0210349 | A1 | 9/2007 | Lu et al. |
| 2010/0163410 | A1* | 7/2010 | Mastromatteo ...... C12Q 1/6825 204/400 |
| 2010/0170324 | A1 | 7/2010 | Mastromatteo et al. |
| 2011/0121916 | A1 | 5/2011 | Barber et al. |
| 2012/0280758 | A1 | 11/2012 | Jaakkola et al. |
| 2012/0319790 | A1 | 12/2012 | Nakamura |
| 2013/0063227 | A1 | 3/2013 | Burak et al. |
| 2015/0293060 | A1 | 10/2015 | Jacobsen |
| 2017/0110300 | A1 | 4/2017 | McCarron et al. |
| 2017/0117871 | A1 | 4/2017 | Rivas et al. |
| 2017/0134001 | A1 | 5/2017 | Belsick et al. |
| 2018/0034438 | A1 | 2/2018 | Ryder et al. |

FOREIGN PATENT DOCUMENTS

| | | |
|---|---|---|
| EP | 2 204 641 A1 | 7/2010 |
| JP | 1997512345 | 12/1997 |
| JP | 2005533265 | 11/2005 |
| JP | 2012116736 | 6/2012 |
| WO | 2004/017063 | 2/2004 |
| WO | WO 2006/063437 A1 | 6/2006 |
| WO | WO 2007/123539 A1 | 11/2007 |

OTHER PUBLICATIONS

U.S. Appl. No. 15/334,511, filed Oct. 26, 2016, Rivas et al.
U.S. Appl. No. 15/334,528, filed Oct. 26, 2016, Belsick et al.
U.S. Appl. No. 15/334,482, filed Oct. 26, 2016, Ryder et al.
U.S. Appl. No. 62/246,302, filed Oct. 26, 2015, Rivas et al.
U.S. Appl. No. 62/252,402, filed Nov. 6, 2015, Belsick et al.
U.S. Appl. No. 62/367,211, filed Jul. 27, 2016, Ryder et al.
PCT/US2016/058745, Oct. 26, 2016, Qorvo US, Inc.
International Patent Application No. PCT/US2016/058745, filed Oct. 26, 2016; International Search Report / Written Opinion dated Feb. 1, 2017; 13 pages.
International Patent Application No. PCT/US2016/058749, filed Oct. 26, 2016, International Search Report / Written Opinion dated Apr. 20, 2017; 16 pages.
Bjurström, et al., "Design and Fabrication of Temperature Compensated Liquid FBAR Sensors," *2006 IEEE Ultrasonics Symposium*, Oct. 2-6, 2006, pp. 894-897.
Brand, et al., "Resonant MEMS: Fundamentals, Implementation and Application", *Advanced Micro & Nanosystems*, series ed. Brand, et al., 2015, John Wiley & Sons, Inc., pp. 370-371.
Canaria, et al., "Formation and removal of alkylthiolate self-assembled monolayers on gold in aqueous solutions", 2006, *Lab on a Chip*, 6(2):289-295. Published online Jan. 3, 2006.
Choi, et al., "A regenerative biosensing surface in microfluidics using electrochemical desorption of short-chain self-assembled monolayer", 2009, *Microfluidics and Nanofluidics*, Springer-Verlag, 7(6): 9 pages. Published online Apr. 10, 2009.
Ferrari, et al., Chapter 2, "Overview of Acoustic-Wave Microsensors", *Piezoelectric Transducers and Applications*, Springer-Verlag, Berlin Heidelberg, 2008, pp. 39-62.
Garcia-Gancedo, et al., "AlN-based BAW resonators with CNT electrodes for gravimetric biosensing", Dec. 15, 2011, *Sensors and Actuators B: Chemical*, 160(1):1386-1393.
Hohmann, et al., "Surface Acoustic Wave (SAW) Resonators for Monitoring Conditioning Film Formation", 2015, *Sensors*, 15(5):11873-11888. Published online May 21, 2015.
Lange, et al., "Surface acoustic wave biosensors: a review", 2008, *Analytical and Bioanalytical Chemistry*, 391:1509-1519. Published online Feb. 12, 2008.
Love, et al., "Self-Assembled Monolayers of Thiolates on Metals as a Form of Nanotechnology", 2005, *Chemical Reviews*, 105(4):1103-1169. Published online Mar. 25, 2005.
Luo, et al., Chapter 21, "Acoustic Wave Based Microfluidics and Lab-on-a-Chip," *Modeling and Measurement Methods for Acoustic Waves and for Acoustic Microdevices*, InTech, Aug. 28, 2013, pp. 515-556.
Mecea, "From Quartz Crystal Microbalance to Fundamental Principles of Mass Measurements", 2005, *Analytical Letters*, 38:753-767.
Mehdizadeh, et al., "Microelectromechanical disk resonators for direct deletion of liquid-phase analytes", 2014, *Sensors and Actuators A: Physical*, 216:136-141. Published online Jun. 2, 2014.
Onen, et al., "Surface Modification on Acoustic Wave Biosensors for Enhanced Specificity," 2012, *Sensors*, 12(9):12317-12328. Published online Sep. 10, 2012.
Plueddemann, *Silane Coupling Agents*, Springer Science+Business Media, New York, New York, 1991, p. 31.
Tencer, et al., "A contact angle and ToF-SIMS study of SAM-thiol interactions on polycrystalline gold", Feb. 15, 2011, *Applied Surface Science*, 257(9):4038-4043. Published online Dec. 4, 2010.
Villa-López, et al., "Design and modelling of solidly mounted resonators for low-cost particle sensing", 2016, *Measurement Science and Technology*, 27(2): 13 pages. Published online Dec. 15, 2015.
Voiculescu, et al., "Acoustic wave based MEMS devices for biosensing applications", 2012, *Biosensors and Bioelectronics*, 33:1-9. Published online Jan. 16, 2012.
Willey, et al., "Rapid Degeneration of Alkanethiol-Based Self-Assembled Monolayers on Gold in Ambient Laboratory Conditions", Aug. 3, 2004, *Surface Science*, Preprint submitted to Elsevier Science, 576(1): 23 pages.
Wingqvist, et al., "Shear mode AlN thin film electro-acoustic resonant sensor operation in viscous media", 2007, *Sensors and Actuators B*, 123:466-473. Published online Nov. 2, 2006.
Zhang, et al., "A single-chip biosensing platform integrating FBAR sensor with digital microfluidic device", *2014 IEEE International Ultrasonics Symposium Proceedings*, 2014, 3 pages.
Qorvo US, Inc., "Summary of Sales Activity of Predecessor To Applicant Concerning Tilted C-Axis Aluminum Nitride Products," Unpublished, Jan. 10, 2017, 1 page.
Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

(56) References Cited

OTHER PUBLICATIONS

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Glass, Nick R. et al., "Organosilane deposition for microfluidic applications," Biomicrofluidics, vol. 5, No. 3, Aug. 16, 2011, pp. 036501-1 to 036501-7.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Jiang, Xingyu et al., "Electrochemical Desorption of Self-Assembled Monolayers Noninvasively Releases Patterned Cells from Geometrical Confinements," Journal of the American Chemical Society, vol. 125, No. 9, Feb. 6, 2003, pp. 2366-2367.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Montagut, Yeison et al., "QCM Technology in Biosensors," Biosensors—Emerging Materials and Applications, Chapter 9, 2011, INTECH Open Access Publisher, pp. 153-178.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Muskal, Nechama et al., "The Electrochemistry of Thiol Self-Assembled Monolayers (SAMs) on a Hanging Mercury Drop Electrode (HMDE)," Current Separations, vol. 19, No. 2, 2000, pp. 49-54.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Ward, Michael D. et al., "Radial Mass Sensitivity of the Quartz Crystal Microbalance in Liquid Media," Analytical Chemistry, vol. 63, No. 9, May 1, 1991, pp. 886-890.

Ye, Tao et al., "Photoreactivity of Alkylsiloxane Self-Assembled Monolayers on Silicon Oxide Surfaces," Langmuir, vol. 17, No. 15, Jun. 21, 2001, pp. 4497-4500.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Yuan, Mingquan et al., "A Method for Removing Self-Assembled Monolayers on Gold," Langmuir, vol. 24, No. 16, Jun. 27, 2008, pp. 8707-8710.

Zhang, X. et al., "Excimer laser ablation of thin gold films on a quartz crystal microbalance at various argon background pressures," Applied Physics A, vol. 64, No. 6, Jun. 1997, pp. 545-552.

Zhou, Yan et al., "Interfacial Structures and Properties of Organic Materials for Biosensors: An Overview," Sensors, vol. 12, Nov. 6, 2012, pp. 15036-15062.

Mooney, J. F. et al., "Patterning of functional antibodies and other proteins by photolithography of silane monolayers," Proceedings of the National Academy of Sciences, vol. 93, No. 22, Oct. 29, 1996, pp. 12287-12291.

Office action with translation dated Sep. 15, 2020 from Japanese Application No. 2019-507805, 8 pages.

\* cited by examiner

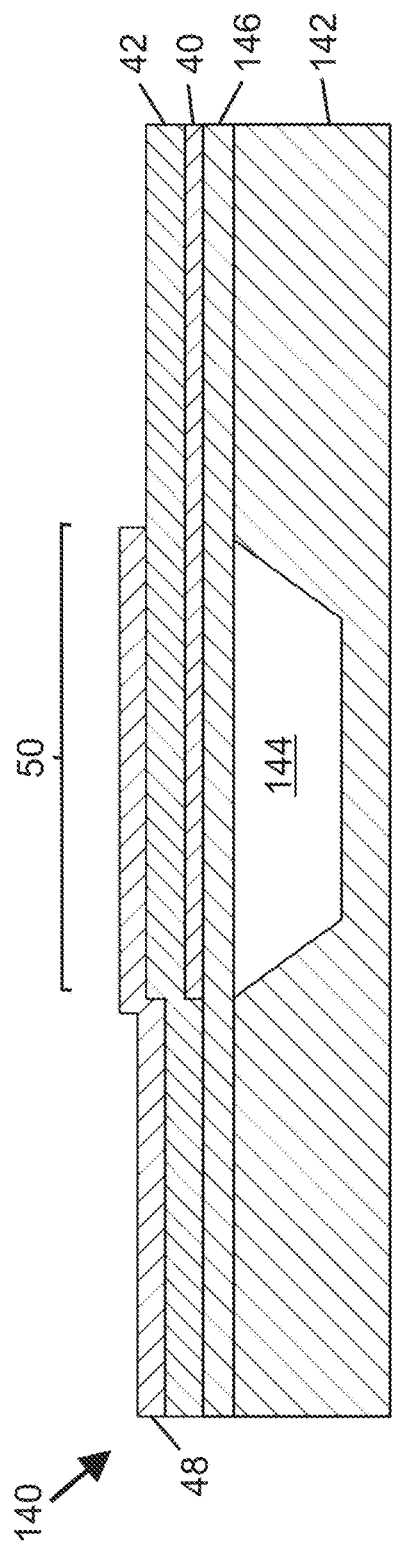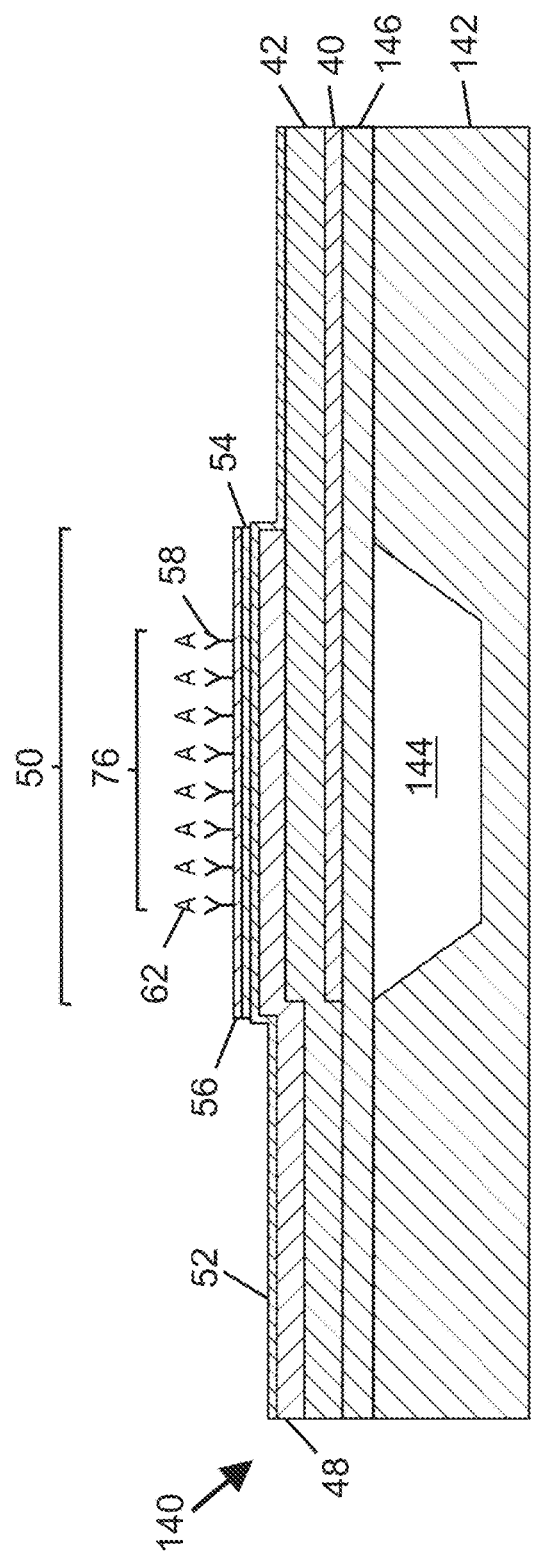

ACOUSTIC RESONATOR DEVICE WITH CONTROLLED PLACEMENT OF FUNCTIONALIZATION MATERIAL

STATEMENT OF RELATED APPLICATIONS

This application is a non-provisional of U.S. provisional patent application Ser. No. 62/373,668, filed Aug. 11, 2016, the disclosure of which is hereby incorporated herein by reference in its entirety. Subject matter disclosed herein also relates to the following three U.S. patent applications each filed or to be filed on Oct. 26, 2016: (1) U.S. patent application Ser. No. 15/334,511 entitled "Acoustic Resonator Devices and Methods Providing Patterned Functionalization Areas;" (2) U.S. patent application Ser. No. 15/334,482 entitled "Acoustic Resonator Devices and Methods with Noble Metal Layer for Functionalization;" and (3) U.S. patent application Ser. No. 15/334,528 entitled "Acoustic Resonator Devices and Fabrication Methods Providing Hermeticity and Surface Functionalization;" wherein the contents of the foregoing three U.S. patent applications are hereby incorporated by reference as if set forth fully herein.

TECHNICAL FIELD

The present disclosure relates to acoustic resonator devices, including acoustic wave sensors and fluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods used with biosensors may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the acoustic wave device and can be correlated to a physical quantity being measured.

In the case of a piezoelectric crystal resonator, an acoustic wave may embody either a bulk acoustic wave (BAW) propagating through the interior of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength.

BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material layer arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof. Conversely, a piezoelectric material grown with a c-axis orientation that is perpendicular relative to a face of an underlying substrate will exhibit a dominant longitudinal response upon application of an alternating current signal across electrodes thereof.

Typically, BAW devices are fabricated by micro-electro-mechanical systems (MEMS) fabrication techniques, owing to the need to provide microscale features suitable for facilitating high-frequency operation. In the context of biosensors, functionalization materials (e.g., specific binding materials, also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing. Unfortunately, dimensional tolerances for microarray spotting are typically larger than dimensional tolerances enabled by MEMS fabrication techniques. An excess of specific binding material may reduce sensor response, such as by impairing a lower limit of detection. Separately, an excess of exposed non-specific binding material may lead to undesirable attachment of analyte when a device is in use.

When analytes are present in very low concentrations in fluid samples, and sensitivity to changes in adsorbed mass is non-uniform with respect to position over the surface of an active region of a MEMS resonator-based biosensor, it may be difficult to reliably promote high sensitivity to changes in adsorbed mass. Restated, it may be difficult to provide a large signal change from a small change in adsorbed mass. Such difficulty may be exacerbated when an analyte-containing fluid sample is supplied parallel to an upper surface of a top side electrode of a biosensor.

Accordingly, there is a need for MEMS resonators employing functionalization material, as well as fluidic devices and methods utilizing such resonators, that are capable of reliably providing enhanced sensitivity to adsorbed mass, and that are suitable for operation in the presence of analyte-containing fluid (e.g., liquid) samples for biosensing or biochemical sensing applications.

SUMMARY

The present disclosure provides a micro-electrical-mechanical system (MEMS) resonator device that is arranged over a substrate and that includes at least one functionalization material arranged over at least a central portion, but less than an entirety, of a top side electrode. For an active region that exhibits greatest sensitivity at a center point and reduced sensitivity along its periphery, omitting functionalization material over at least one peripheral portion of a resonator active region prevents analyte binding in regions of lowest sensitivity. Restated, providing functionalization material solely over a central portion of the resonator active region that exhibits greatest sensitivity provides a larger signal change from smaller changes in mass adsorbed by binding to the functionalization material. This may be particularly beneficial when a MEMS resonator-based sensing device is used with fluid samples containing analytes at very low concentrations. Adjusting dimensions and configuration of an area containing functionalization material relative to the active area may also enhance sensor response. For example, at least one functionalization material may extend a maximum length in a range of from about 20% to about 95% (or in subranges of from about 30% to about 95%, or from about 40% to about 90%, or from about 50% to about 90%) of an active area length and may extend a maximum width in a range of from about 50% to 100% (or in subranges of from about 60% to about 100%, or from about 70% to about 95%) of an active area width. When such a MEMS resonator device is incorporated into a fluidic device, directionality of an area containing functionalization material relative to a direction of analyte-containing fluid flow may also be selected to enhance sensor response, which may be important when an analyte is present at a very low concentration.

In one aspect, the disclosure relates to a micro-electrical-mechanical system (MEMS) resonator device including a substrate, a bulk acoustic wave resonator structure arranged over at least a portion of the substrate, and at least one functionalization material arranged over at least a central portion of a top side electrode. The bulk acoustic wave resonator structure includes a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region. The top side electrode includes an active area portion that overlaps the bottom side electrode and is coincident with the active region, the active area portion includes an active area width, and the active area portion includes an active area length extending perpendicular to the active area width. The at least one functionalization material extends a maximum length in a range of from about 20% to about 95% (or in subranges of from about 30% to about 95%, or from about 40% to about 90%, or from about 50% to about 90%) of the active area length and extends a maximum width in a range of from about 50% to 100% (or in subranges of from about 60% to about 100%, or from about 70% to about 95%) of the active area width.

In certain embodiments, the maximum width of the at least one functionalization material exceeds the maximum length thereof.

In certain embodiments, the MEMS resonator device further includes a self-assembled monolayer (SAM) arranged between the top side electrode and the at least one functionalization material. In certain embodiments, the MEMS resonator device further includes an interface layer (e.g., including an oxide layer, a nitride, or an oxynitride material) arranged between the top side electrode and the at least one functionalization material.

In certain embodiments, the top side electrode comprises a non-noble metal, and the MEMS resonator device further includes a hermeticity layer arranged between the interface layer and the top side electrode. If provided, a hermeticity layer preferably includes a dielectric material with a low water vapor transmission rate (e.g., no greater than 0.1 $g/m^2/day$). In certain embodiments, a self-assembled monolayer is arranged between the interface layer and the at least one functionalization material. In certain embodiments, the MEMS resonator device further includes a blocking layer arranged over a portion of the piezoelectric material non-coincident with the active region, wherein the presence of the blocking layer may serve to prevent binding of one or more species.

In certain embodiments, the at least one functionalization material comprises a specific binding material. In certain embodiments, the at least one functionalization material comprises a non-specific binding material.

In certain embodiments, the piezoelectric material comprises a c-axis having an orientation distribution that is predominantly non-parallel to normal of a face of the substrate.

In certain embodiments, the MEMS resonator device further includes at least one acoustic reflector element arranged between the substrate and the bulk acoustic wave resonator structure, such as to form a solidly mounted resonator structure. In other embodiments, the substrate defines a recess, and the MEMS resonator device further comprises a support layer arranged between the bulk acoustic wave resonator structure and the recess, wherein the active region is arranged over at least a portion of the support layer and at least a portion of the recess, such as to form a film bulk acoustic resonator (FBAR) structure.

In another aspect, the disclosure relates to a sensor and/or a fluidic device including a MEMS resonator device as disclosed herein. In one embodiment, a fluidic device comprising a MEMS resonator device includes a fluidic passage containing the active region and arranged to conduct a flow of liquid to contact the at least one functionalization material, wherein the fluidic passage is arranged to conduct the flow of liquid from an inlet port upstream of the active region toward the active region in a direction that is substantially parallel to the active area length. In certain embodiments, the at least one functionalization material is arranged in a shape comprising a leading edge (which may be straight, curved, angled, sawtooth, or another suitable shape), wherein a center point of the leading edge is arranged between the inlet port and a center point of the active region.

In another aspect, the disclosure relates to a method for biological or chemical sensing including a fluidic device as disclosed herein. One method step includes supplying a fluid containing a target species into the fluidic passage of the fluidic device, wherein said supplying is configured to cause at least some of the target species to bind to the at least one functionalization material. Additional method steps include inducing a bulk acoustic wave in the active region, and sensing a change in at least one of a frequency property, a magnitude property, or a phase property of the bulk acoustic wave resonator structure to indicate at least one of presence or quantity of target species bound to the at least one functionalization material.

In another aspect, the disclosure relates to a method for fabricating a micro-electrical-mechanical system (MEMS) resonator device. One method step includes forming a bulk acoustic wave resonator structure including a piezoelectric material, a top side electrode arranged over a portion of the piezoelectric material, and a bottom side electrode arranged between the piezoelectric material and a substrate, wherein a portion of the piezoelectric material is arranged between the top side electrode and the bottom side electrode to form an active region, the top side electrode comprises an active area portion that overlaps the bottom side electrode and is coincident with the active region, the active area portion includes an active area width, and the active area portion includes an active area length extending perpendicular to the active area width. Another method step includes depositing at least one functionalization material arranged over at least a central portion of the top side electrode, wherein the at least one functionalization material extends a maximum length in a range of from about 20% to about 95% (or in subranges of from about 30% to about 95%, or from about 40% to about 90%, or from about 50% to about 90%) of the active area length and extends a maximum width in a range of from about 50% to 100% (or in subranges of from about 60% to about 100%, or from about 70% to about 95%) of the active area width.

In certain embodiments, the foregoing method further includes forming a self-assembled monolayer over at least a portion of the top side electrode prior to said depositing of the at least one functionalization material, wherein the at least one functionalization material is arranged over at least a portion of the self-assembled monolayer. In certain embodiments, the forming of a self-assembled monolayer over at least a portion of the top side electrode comprises multiple steps, including (i) applying the self-assembled monolayer over the top side electrode; (ii) arranging a first mechanical mask over the self-assembled monolayer, wherein the first mechanical mask defines at least one first aperture through which at least one first portion of the self-assembled monolayer is exposed; and (iii) transmitting electromagnetic radiation comprising a peak wavelength in a range of from about 150 nm to 400 nm through the at least one first aperture to interact with the at least one first portion of the self-assembled monolayer to promote removal of the at least one first portion of the self-assembled monolayer. In certain embodiments, a method further includes arranging a second mechanical mask over at least a portion of the bulk acoustic wave resonator structure including the active region, wherein the second mechanical mask defines at least one second aperture through which at least one second portion of the self-assembled monolayer is exposed; and applying a blocking layer through the at least one second aperture to the at least one second portion of the self-assembled monolayer. Certain embodiments further include a step of forming at least one wall over a portion of the bulk acoustic wave resonator structure and defining a fluidic passage overlying the active region, wherein the fluidic passage is arranged to conduct a flow of liquid from an inlet port upstream of the active region toward the active region in a direction that is substantially parallel to the active area length, and the fluidic passage is arranged to conduct the flow of liquid to contact the at least one functionalization material.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 15 is a schematic cross-sectional view of a film bulk acoustic wave resonator (FBAR) structure usable in devices according to certain embodiments disclosed herein, with the FBAR structure including an inclined c-axis hexagonal crystal structure piezoelectric material, a substrate defining a cavity covered by a support layer, and an active region registered with the cavity, with a portion of the piezoelectric material arranged between overlapping portions of a top side electrode and a bottom side electrode.

FIG. 16 is a schematic cross-sectional view of a FBAR structure according to FIG. 15, following addition of a hermeticity layer, an interface layer, a self-assembled monolayer, and a functionalization material (e.g., specific binding material) over at least portions of the FBAR structure

DETAILED DESCRIPTION

Figure 1A:
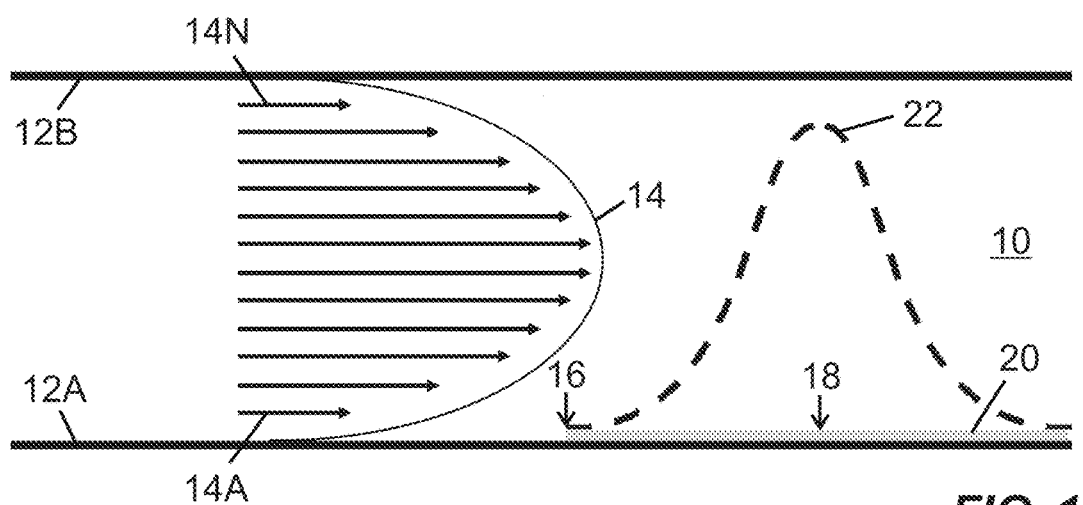
FIG. 1A is a side cross-sectional schematic representation of a fluidic passage containing an active region of a BAW MEMS resonator structure overlaid with functionalization material, showing a Gaussian sensitivity profile superimposed over the active region, and showing streamlines of a front of fluid advancing in a left-to-right direction in the fluidic passage transverse to normal of an upper surface of the active region.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides a micro-electrical-mechanical system (MEMS) resonator device that is arranged over a substrate and that includes at least one functionalization material arranged over at least a central portion, but less than an entirety, of a top side electrode. For an active region that exhibits greatest sensitivity at a center point and reduced sensitivity along its periphery, omitting functionalization material over at least one peripheral portion of a resonator active region prevents analyte binding in regions of lowest sensitivity. Adjusting dimensions and configuration of an area containing functionalization material relative to the active area may also enhance sensor response. For example, at least one functionalization material may extend a maximum length in a range of from about 20% to about 95% (or in subranges of from about 30% to about 95%, or from about 40% to about 90%, or from about 50% to about 90%) of an active area length and extend a maximum width in a range of from about 50% to 100% (or in subranges of from about 60% to about 100%, or from about 70% to about 95%) of an active area width.

Quartz microbalances are known to exhibit a frequency response that changes as a Gaussian function of distance from the center (i.e., with the center point exhibiting the highest sensitivity to changes in mass, and with sensitivity declining away from the center). See, e.g., S. Zhang, et al., *Appl. Phys.* A 64, 545-552 (1997). Applicant has postulated that a similar phenomenon may apply to bulk acoustic wave MEMS resonator-based sensors and fluidic devices incorporating such sensors as disclosed herein for biosensing or biochemical sensing applications. When concentration of analyte in a sample is extremely low (e.g., in certain medical diagnostic applications), it may be highly advantageous to allow analyte binding only in the most sensitive region of a resonator-based biochemical sensor device. Restated, it may be highly advantageous to avoid analyte binding in insensitive or relatively insensitive regions, such as regions outside a sensor active area, as well as regions of a sensor active area exhibiting low sensitivity to changes in adsorbed mass.

Figure 1B:
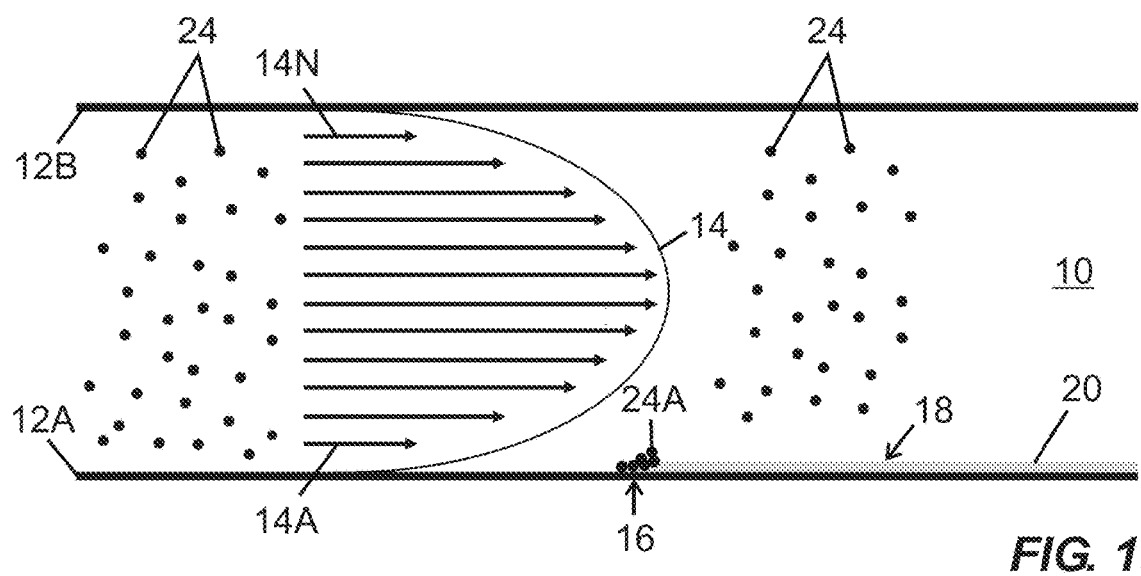
FIG. 1B is a side cross-sectional schematic representation of the fluidic passage, active region, and advancing front of fluid of FIG. 1A, further depicting distributions of analyte upstream and downstream of the active region, with an accumulation of analyte proximate to a radial boundary of the active region upstream of a center point of the active region.
Figure 1C:
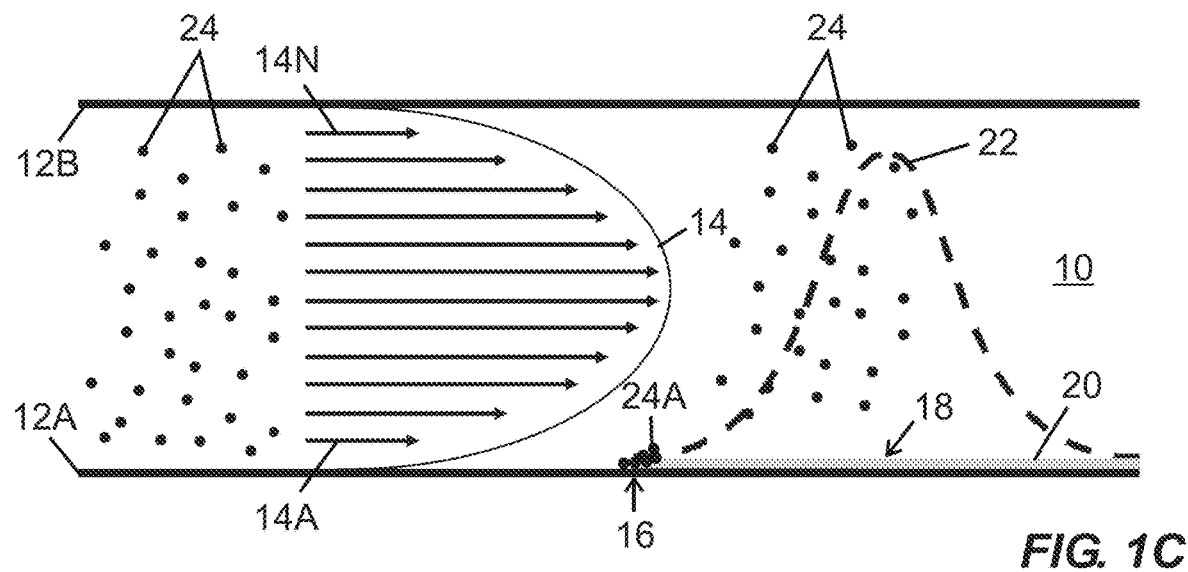
FIG. 1C is a side cross-sectional schematic representation of the fluidic passage, active region, advancing front of fluid, analyte distributions, and analyte accumulation of FIG. 1B, with the Gaussian sensitivity profile of FIG. 1A superimposed over the active region.

FIGS. 1A-1C provide side cross-sectional schematic representations of a fluidic passage 10 containing an active region 20 of a BAW MEMS resonator device, with the active region 20 including functionalization material arranged thereon. The fluidic passage 10 may be microfluidic in character. In FIG. 1A, a Gaussian sensitivity profile 22 is superimposed over the active region 20, showing maximum sensitivity over a center point 18 of the active region 20, and showing sensitivity reducing in a curvilinear fashion away from the center point 18 (e.g., exhibiting minimum sensitivity at peripheral edges, such as a leading edge 16). The fluidic passage 10 includes lower and upper boundaries 12A, 12B containing an advancing front of fluid 14 in laminar flow conditions (such as experienced in microfluidic channels, also known as microchannels). The advancing front of fluid 14 may be represented as fluid following parallel streamline paths 14A-14N, with lower velocities proximate to the lower and upper boundaries 12A, 12B, and comparatively higher velocities at medial portions of the fluidic passage 10 between the boundaries 12A, 12B. When the advancing front of fluid 14 flows over the active region 20, portions of the fluid proximate to a lower streamline path 14A are subject to interaction with the active region 20.

Although not shown in FIG. 1A, fluid within the fluidic passage 10 may include at least one analyte subject to interaction with the active region 20. FIG. 1B shows the fluidic passage 10, active region 20, and advancing front of fluid 14 of FIG. 1A, and further depicts distributions of analyte 24 upstream and downstream of the leading edge 16 of the active region 20. When the advancing front of fluid 14 flows over the active region 20, analyte 24 contained in fluid proximate to the lower boundary 12A may bind with functionalization material of the active region 20. If the functionalization material is distributed over the entire active region 20, then analyte 24 contained in the fluid proximate to the lower streamline path 14A is likely to bind the first functionalization material it contacts, thereby forming an analyte accumulation 24A proximate to the leading edge 16 of the active region 20. Unfortunately, portions of the active region 20 proximate to the leading edge 16 are significantly less sensitive to changes in adsorbed mass than the center point 18 of the active region, as shown in FIG. 1C (which provides the same content as FIG. 1B, but with the Gaussian sensitivity profile 22 of FIG. 1A superimposed over the active region 20).

Fluids in laminar flow tend to follow parallel streamline paths, such that the chaotic fluctuations of velocity that tend to homogenize fluids in turbulent flows are absent. Multiple fluids introduced in a standard microchannel generally will not mix with each other, except at a common interface between the fluids via diffusion, and the diffusion process is typically slow compared with the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Fick's first law of diffusion states that flux moves from regions of high concentration to regions of low concentration. Secondarily, the flux rate is proportional to the concentration gradient difference.

Referring to FIGS. 1B and 1C, the advancing front of fluid 14 containing analyte 24 may be modeled as a moving "stack" of horizontal fluid layers (e.g., corresponding to streamline paths 14A-14N). Even if it is assumed that analyte concentration is constant in each layer of the stack forming the fluid volume upstream of the active region 20, following passage of the fluid volume over functionalization material overlying the active region 20, one or more lowermost fluid layers of the stack will exhibit reduced or depleted analyte concentration due to binding of analyte 24 with the functionalization material (e.g., shown by the analyte accumulation 24A in FIGS. 1B and 1C). But since diffusion is slow in a direction perpendicular to the direction of fluid flow through the fluidic passage 10, and analyte 24 needs to diffuse to the functionalization material overlying the active region 20 to bind, analyte 24 present in fluid layers other than the lowermost fluid layer(s) may not be available for binding with the functionalization material of the active region 20 within a reasonable period of time. Thus, concentration of analyte 24 may remain stratified within the fluidic passage 10 until diffusion occurs. As a result, when analyte 24 present in the lowermost fluid layer(s) of the advancing front of fluid 14 binds with functionalization material arranged along the leading edge 16 of the active region 20, the analyte accumulation 24A may form proximate to the leading edge 16, but very little analyte binding may occur proximate to the center point 18 of the active region 20. Given the Gaussian sensitivity profile 22, presence of analyte accumulation 24A at the leading edge 16 of the active region 20 in combination with an absence of analyte bound to functionalization material proximate to the center point 18 of the active region 20 will result in limited (low) aggregate response for a sensor incorporating the active region 20.

As noted previously, adjusting dimensions and configuration of an area containing functionalization material relative to the active area may enhance sensor response. For example, at least one functionalization material may extend a maximum length in a range of from about 20% to about 95% (or in subranges of from about 30% to about 95%, or from about 40% to about 90%, or from about 50% to about 90%) of an active area length and extend a maximum width in a range of from about 50% to 100% (or in subranges of from about 60% to about 100%, or from about 70% to about 95%) of an active area width. Methods for applying at least one functionalization material over less than an entirety of an active area may include, but are not limited to, one or more of: patterning a functionalization material using one or more mechanical masks or patterned photoresist layers over one or more regions of an active area; patterning an interface layer (arranged to underlie and receive a functionalization material) over one or more regions of an active area; or patterning a blocking material (arranged to prevent binding of functionalization material and/or analyte) over one or more regions of an active area. Through use of such methods, functionalization material may be applied and/or rendered available for analyte binding at a higher dimensional tolerance than could be attained by microarray spotting alone.

Before describing methods for applying at least one functionalization material over less than an entirety of an active area of a resonator device, exemplary bulk acoustic wave MEMS resonator devices, associated layers useful for providing biochemical sensing utility, and fluidic devices incorporating MEMS resonator devices will be introduced.

A preferred micro-electrical-mechanical system (MEMS) resonator device according to certain embodiments includes a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with an active region of a BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material.

Figure 2:
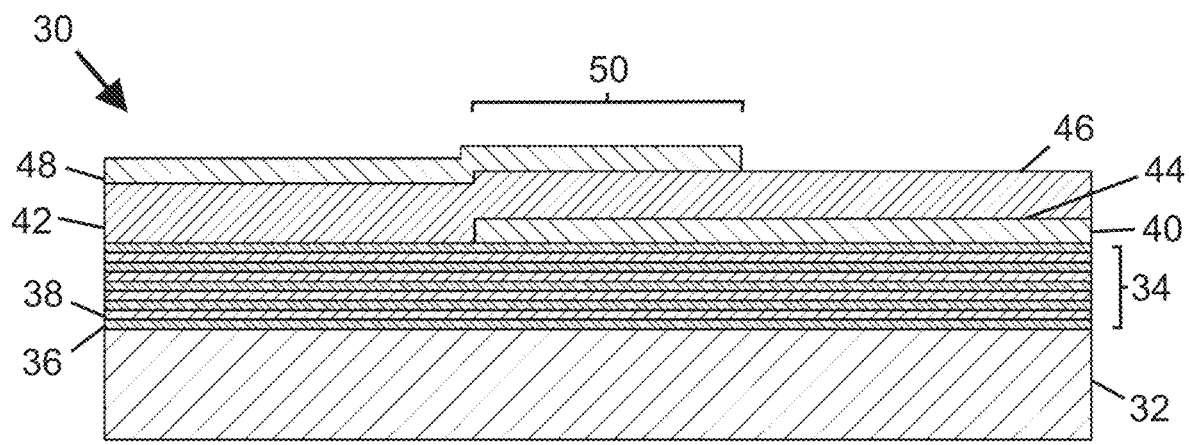
FIG. 2 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

FIG. 2 is a schematic cross-sectional view of a portion of a bulk acoustic wave MEMS resonator device 30 useable with embodiments disclosed herein. The resonator device 30 includes a substrate 32 (e.g., typically silicon or another semiconductor material), an acoustic reflector 34 arranged over the substrate 32, a piezoelectric material 42, and bottom and top side electrodes 40, 48. The bottom side electrode 40 is arranged along a portion of a lower surface 44 of the piezoelectric material 42 (between the acoustic reflector 34 and the piezoelectric material 42), and the top side electrode 48 is arranged along a portion of an upper surface 46 of the piezoelectric material 42. An area in which the piezoelectric material 42 is arranged between overlapping portions of the top side electrode 48 and the bottom side electrode 40 is considered an active region 50 of the resonator device 30. The acoustic reflector 34 serves to reflect acoustic waves and therefore reduce or avoid their dissipation in the substrate 32. In certain embodiments, the acoustic reflector 34 includes alternating thin layers 36, 38 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 32. In certain embodiments, other types of acoustic reflectors may be used. Steps for forming the resonator device 30 may include depositing the acoustic reflector 34 over the substrate 32, followed by deposition of the bottom side electrode 40, followed by growth (e.g., via sputtering or other appropriate methods) of the piezoelectric material 42, followed by deposition of the top side electrode 48.

In certain embodiments, the piezoelectric material 42 comprises a hexagonal crystal structure piezoelectric material (e.g., aluminum nitride or zinc oxide) that includes a c-axis having an orientation distribution that is predominantly non-parallel (and may also be non-perpendicular to) to normal of a face of the substrate 32. Under appropriate conditions, presence of a c-axis having an orientation distribution that is predominantly non-parallel to normal of a face of a substrate enables a BAW resonator structure to be configured to exhibit a dominant shear response upon application of an alternating current signal across a distal electrode and a proximal electrode thereof (e.g., as may be desirable in the context of a BAW resonator structure providing sensing utility). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

The bulk acoustic wave MEMS resonator device 30 shown in FIG. 2 lacks any layers (e.g., including functionalization material) overlying the active region 50 that would permit the resonator device 30 to be used as a biochemical sensor. If desired, at least portions of the resonator device 30 shown in FIG. 2 (e.g., including the active region 50) may be overlaid with various layers, such as one or more of: a hermeticity layer, an interface layer, a self-assembled monolayer (SAM), and/or a functionalization material layer (which may include specific binding material or non-specific binding material).

Figure 3:
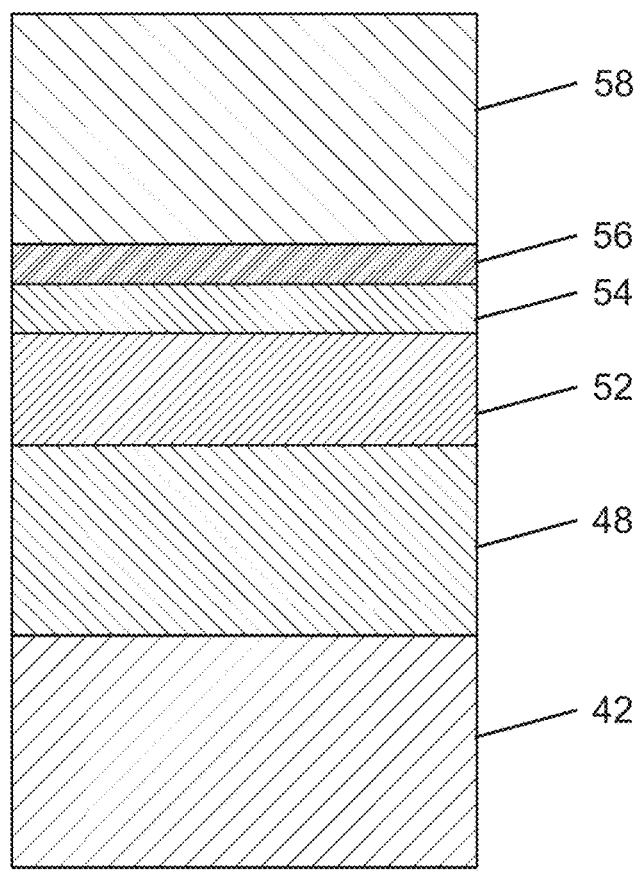
FIG. 3 is a schematic cross-sectional view of an upper portion of a BAW resonator device including a piezoelectric material and a top side electrode overlaid with a hermeticity layer, an interface layer, a self-assembled monolayer, and a functionalization material (e.g., specific binding material).

FIG. 3 is a schematic cross-sectional view of an upper portion of a BAW resonator device including a piezoelectric material 42 and a top side electrode 48 overlaid with a hermeticity layer 52, an interface layer 54, a self-assembled monolayer (SAM) 56, and a functionalization material layer (e.g., specific binding material) 58. In certain embodiments, one or more blocking materials (not shown) may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide ($SiO_2$). Alternative materials incorporating hydroxylated oxide surfaces for forming interface layers include silicon dioxide [$SiO_2$], titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 5 nm to about 100 nm, or from about 5 nm to about 50 nm, or from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 2 nm to about 20 nm, or from about 5 nm to about 15 nm, or from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups— namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one specific binding material. In certain embodiments, specific binding materials may be applied on or over a SAM using a microarray spotting needle or other suitable methods. In certain embodiments, an interface layer may be patterned (e.g., using photolithography for defining the interface layer) with a high dimensional tolerance over only a portion of a resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization material (e.g., chemical functionalization material) may provide non-specific binding utility.

Certain embodiments are directed to a fluidic device including multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the resonator structures. Such a device may be microfluidic in scale, and comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic channel over a first bulk acoustic wave MEMS resonator structure with an active region thereof arranged along a bottom surface of a microfluidic passage, and then enclosing the microfluidic passage using a cap or cover layer that may define fluidic ports (e.g., openings) enabling fluid communication with the microfluidic passages. In certain embodiments, functionalization (e.g., specific binding) material may be pre-applied to the active region of a bulk acoustic wave MEMS resonator structure before formation of a microfluidic passage; in other embodiments, functionalization material may be applied over an active region of a bulk acoustic wave resonator structure following formation of the microfluidic passage.

Walls of a microfluidic channel may be formed of any suitable material, such as laser-cut "stencil" layers of thin polymeric materials and/or laminate materials, optionally including one or more self-adhesive surfaces (e.g., adhesive tape). Optionally such walls may be formed prior to deposition of a SAM layer, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic channel, and the integrally formed partial cover/wall structure may be applied (e.g., adhered or otherwise bonded) over at least a portion of a bulk acoustic wave resonator structure to enclose the at least one fluidic channel.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical blocking material is ideal for every situation, since each antibody-antigen pair has unique characteristics.

Figure 4:
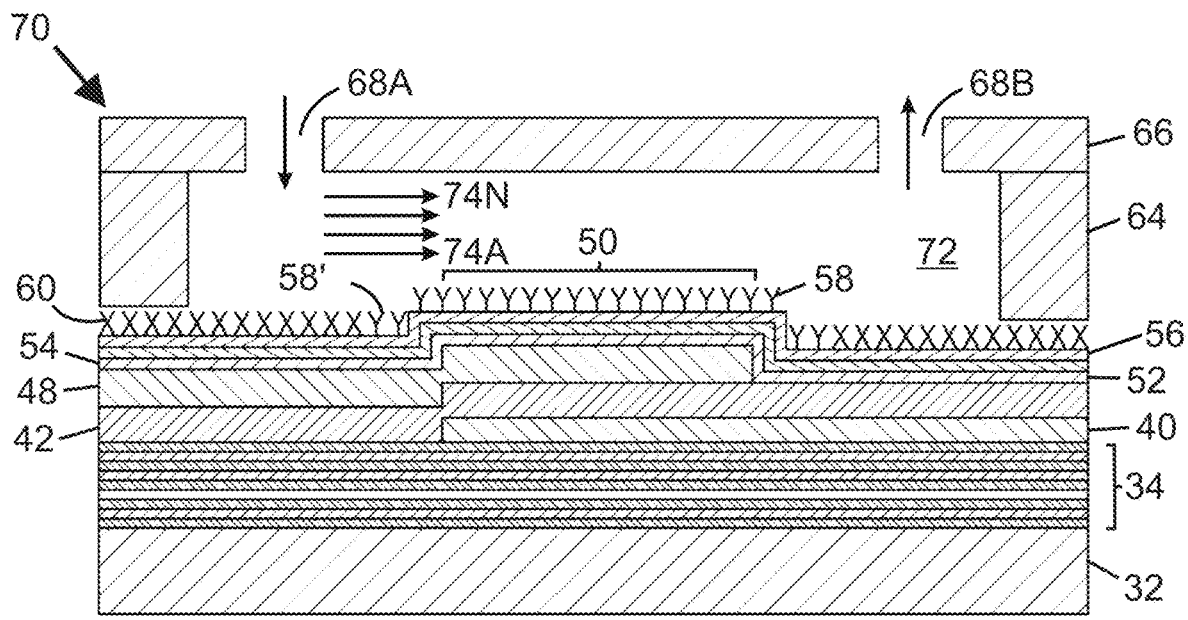
FIG. 4 is a schematic cross-sectional view of a portion of a fluidic device (e.g., a biochemical sensor device) including a fluidic passage bounded from below by a BAW resonator structure overlaid with functionalization material, bounded laterally by walls, and bounded from above by a cover defining fluidic ports, with the functionalization material extending across and beyond the entire active region.

FIG. 4 is a schematic cross-sectional view of a portion of a fluidic device 70 (e.g., a biochemical sensor device) including a microfluidic passage 72 bounded from below by a bulk acoustic wave MEMS resonator structure including an active region 50, bounded laterally by walls 64, and bounded from above by a cover or cap layer 66 defining fluidic ports 68A, 68B to serve as a comparison device intended to provide context for subsequently described embodiments of the present disclosure. The fluidic device 70 includes a substrate 32 overlaid with an acoustic reflector 34, and a bottom side electrode 40 arranged generally below a piezoelectric material 42. A top side electrode 48 extends over a portion of the piezoelectric material 42, wherein a portion of the piezoelectric material 42 arranged between the top side electrode 48 and the bottom side electrode 40 embodies the active region 50 of the BAW MEMS resonator structure. The top side electrode 48 and the piezoelectric material 42 are overlaid with a hermeticity layer 52, an interface layer 54, and a self-assembled monolayer (SAM) 56. Portions of the SAM 56 between the active region 50 and the walls 64 are overlaid with a chemical or biological blocking material 60 to prevent localized attachment of functionalization material and/or analyte. A portion of the SAM 56 that is registered with the active region 50 is overlaid with functionalization (e.g., specific binding) material layer 58 arranged to bind at least one analyte. Walls 64 that are laterally displaced from the active region 50 extend upward from the chemical or biological blocking material 60 to define lateral boundaries of the microfluidic passage 72 containing the active region 50. If the walls 64 are formed on the SAM 56, then the SAM 56 may promote adhesion of the walls 64. The walls 64 may be formed of any suitable material, such as a laser-cut "stencil" layer of thin polymeric materials and/or laminate materials, optionally including one or more self-adhesive surfaces (e.g. adhesive tape). Optionally such walls 64 may be formed prior to deposition of the SAM 56, functionalization material layer 58, and chemical or biological blocking material 60 with an SU-8 negative epoxy resist or other photoresist material. The cover or cap layer 66 defining upper surface fluidic ports 68A, 68B is further provided to provide an upper boundary for the microfluidic passage 72. The cover or cap layer 66 may be formed by defining ports (e.g., via laser cutting or water jet cutting) in a layer of an appropriate material (e.g., a substantially inert polymer, glass, silicon, ceramic, or the like), and adhering the cover or cap layer 66 to top surfaces of the walls 64.

As indicated previously herein, it may be difficult to achieve a high degree of alignment between functionalization material and an active region of a MEMS resonator device through reliance on microarray spotting alone. As shown in FIG. 4, a laterally extending portion 58' of the functionalization material layer 58 extends laterally beyond the active region 50 of the BAW MEMS resonator device, and is available to bind analyte contained in fluid within the microfluidic passage 72. The laterally extending portion 58' of the functionalization material layer 58 constitutes excess functionalization (e.g., specific binding) material that may reduce sensor response, such as by impairing a lower limit of detection by binding analyte supplied to the microfluidic passage 72 before it would otherwise be transported to the active region 50. Even if excess functionalization material were not present beyond a lateral extent of the active region 50, the presence of functionalization material layer 58 over the entire active region 50 might tend to impair a lower limit of detection, due to reduced sensitivity of the active region 50 away from a center point or center region thereof. As described previously in connection with FIGS. 1A-1C, when functionalization material is provided along an entire active region, and analyte-containing fluid is arranged to flow parallel to an upper face of the active region, then analyte may tend to accumulate along a leading edge of the functionalization material proximate to a radial boundary of the active region. The binding of analyte to functionalization material arranged proximate to a radial boundary of an active region may reduce or eliminate the presence of analyte available to bind to functionalization material arranged over a center point or central region of the active region, particularly if the analyte concentration is very low. Given a Gaussian (or similar) sensitivity profile, the presence of analyte accumulation at a leading edge of an active region in combination with an absence of analyte bound to functionalization material proximate to a center point of the active region will result in limited (low) aggregate response for a sensor incorporating the active region.

In use of the fluidic device 70, a fluid sample may be supplied through the first fluidic port 68A into the microfluidic passage 72 over the active region 50 and through the second fluidic port 68B to exit the microfluidic passage 72. Due to the laminar nature of the fluid flow within the microfluidic passage 72, the fluid volume may be modeled and behave as a "stack" of horizontal fluid layers including a lowermost fluid layer 74A and an uppermost fluid layer 74N. An analyte contained in the lowermost fluid layer 74A of the fluid sample will tend to bind with the laterally extending portion 58' of the functionalization material layer 58 arranged upstream of the active region 50 and accumulate at this location. If analyte concentration in the sample is low, then the lowermost fluid layer 74A may be depleted of analyte after binding and accumulation of analyte at a leading edge of functionalization material along a peripheral portion of the active region 50. Analyte contained in fluid layers above the lowermost fluid layer 74A (including the uppermost fluid layer 74N) may not be available to bind with the functionalization material layer 58, since diffusion of analyte (e.g., in a vertical direction) between the fluid layers 74A-74N may occur slowly. As a result, the analyte concentration in the sample may need to be relatively high for any analyte to be available to bind with functionalization material layer 58 arranged over a center point of the active region 50. Assuming that sufficient analyte is present to bind with functionalization material layer 58 arranged over the active region 50, when a bulk acoustic wave is induced in the active region 50 by supplying an electrical (e.g., alternating current) signal to the bottom and top side electrodes 40, 48, a change in at least one of a frequency property, a magnitude property, or a phase property of the BAW resonator structure may be detected to indicate a presence and/or quantity of analyte bound to the functionalization material layer 58. If no analyte is bound to the functionalization material layer 58 near the center point of the active region 50, then the sensor response may be low or difficult to detect.

To overcome limitations associated with presence of functionalization material arranged over peripheral portions of an active area of a resonator (as well as excess functionalization material extending laterally beyond an active area), embodiments disclosed herein limit the presence of functionalization material to less than an entirety of an active region, by omitting functionalization material over at least one peripheral portion of a resonator active region. Methods for limiting the location of functionalization material to less than an entirety of an active region may include, for example: patterning an interface layer over less than an entirety of an active region (e.g., providing an interface layer along a central portion, but not along one or more peripheral portions, of an active region); patterning a blocking layer over one or more peripheral portions of an active region, either over an interface layer or a SAM; patterning a SAM over less than an entirety of an active region; or one or more combinations of the foregoing. As techniques having higher resolution than traditional microarray spotting are developed for depositing functionalization material, such techniques may additionally be used to limit the location of functionalization material to less than an entirety of an active region.

FIGS. 5A-5F illustrate the fabrication of a fluidic device (e.g., a biochemical sensor device) incorporating a bulk acoustic wave MEMS resonator structure according to FIG. 2, with each figure showing the structure after completion of a fabrication step, and with the fluidic device including functionalization material arranged over a central portion, but less than an entirety of, an active region of the BAW resonator structure.

Figure 5A:
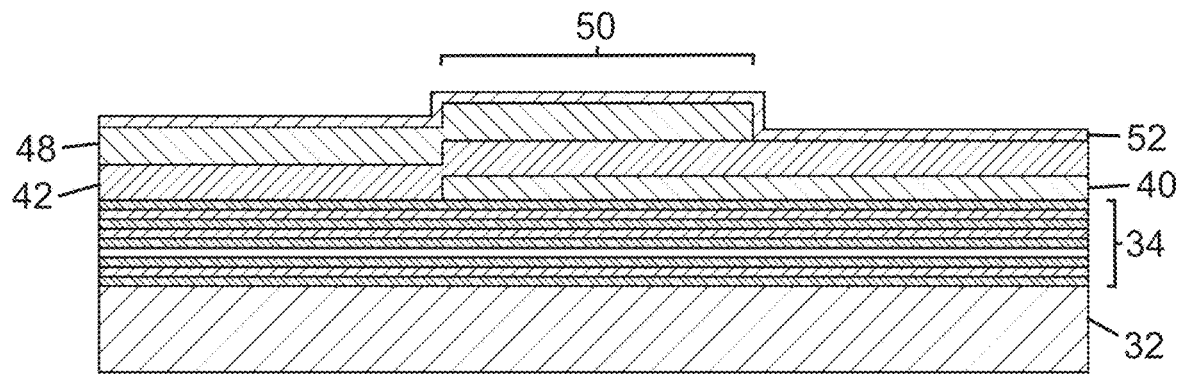
FIGS. 5A-5E provide schematic cross-sectional views of portions of a fluidic device (e.g., a biochemical sensor device) following performance of sequential fabrication steps and incorporating a BAW resonator structure according to FIG. 2.
Figure 5B:
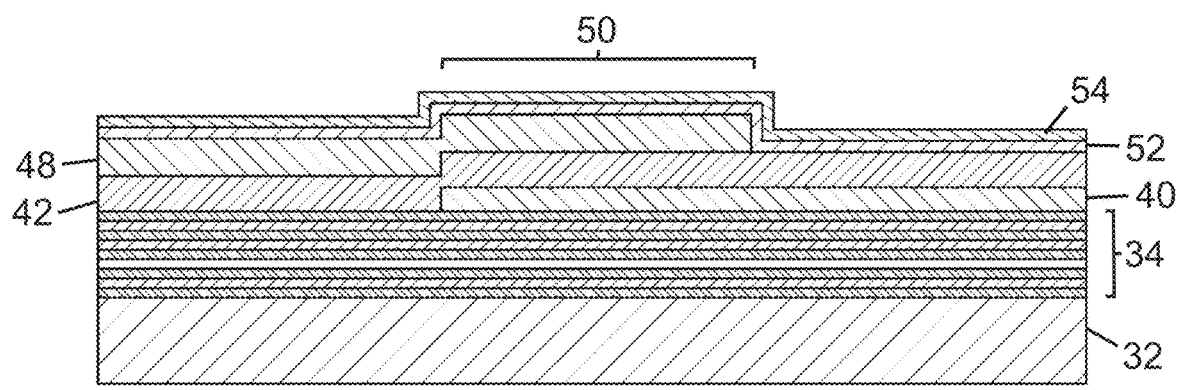
Figure 5C:
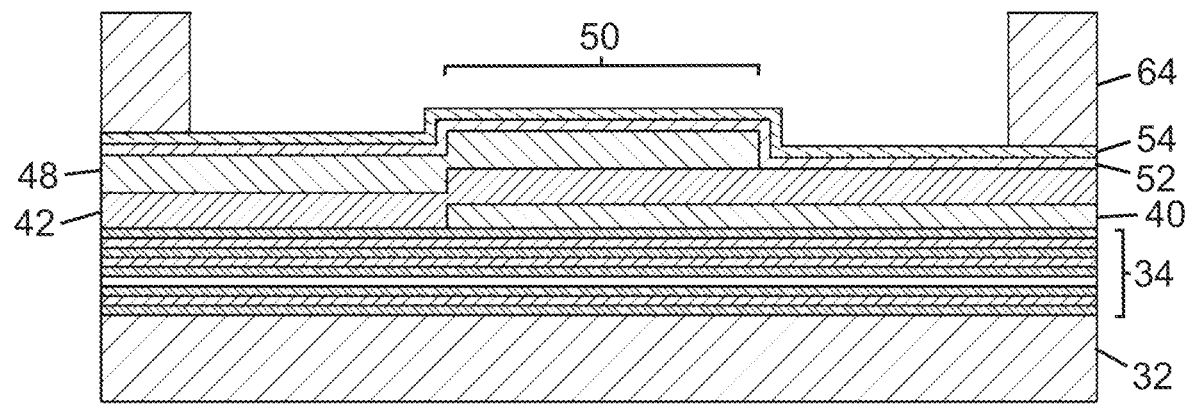

FIG. 5A is a schematic cross-sectional view of a BAW resonator device portion according to FIG. 2 (including a substrate 32, an acoustic reflector 34, a piezoelectric material 42, and bottom and top side electrodes 40, 48), following deposition of a hermeticity layer 52 over surfaces of the top side electrode 48 and the piezoelectric material 42. The hermeticity layer 52 extends over an active region 50 as well as the remainder of the piezoelectric material 42. FIG. 5B illustrates the BAW resonator device portion of FIG. 5A following deposition of an interface layer 54 over the hermeticity layer 52. In certain embodiments, the hermeticity layer 52 and/or the interface layer 54 may be applied via one or more deposition processes such as atomic layer deposition (ALD), chemical vapor deposition (CVD), or physical vapor deposition (PVD), with these layers 52, 54 optionally being sequentially applied in a vacuum environment. The hermeticity layer 52 preferably comprises an oxide, a nitride, or an oxynitride material serving as a dielectric material and having a low water vapor transmission rate. The interface layer 54 preferably comprises a hydroxylated oxide surface, or a gold or other noble metal, suitable for receiving a SAM. FIG. 5C illustrates the BAW resonator device portion of FIG. 5B following formation of walls 64 over the interface layer 54, with the walls 64 being laterally displaced relative to the active region 50, to define lateral boundaries of a microfluidic passage containing the active region 50. Such walls 64 may be formed of any suitable material, such as a laser-cut "stencil" layer of thin polymeric materials and/or laminate materials, optionally including one or more self-adhesive surfaces (e.g. adhesive tape), or using an SU-8 negative epoxy resist or other photoresist material.

Figure 5D:
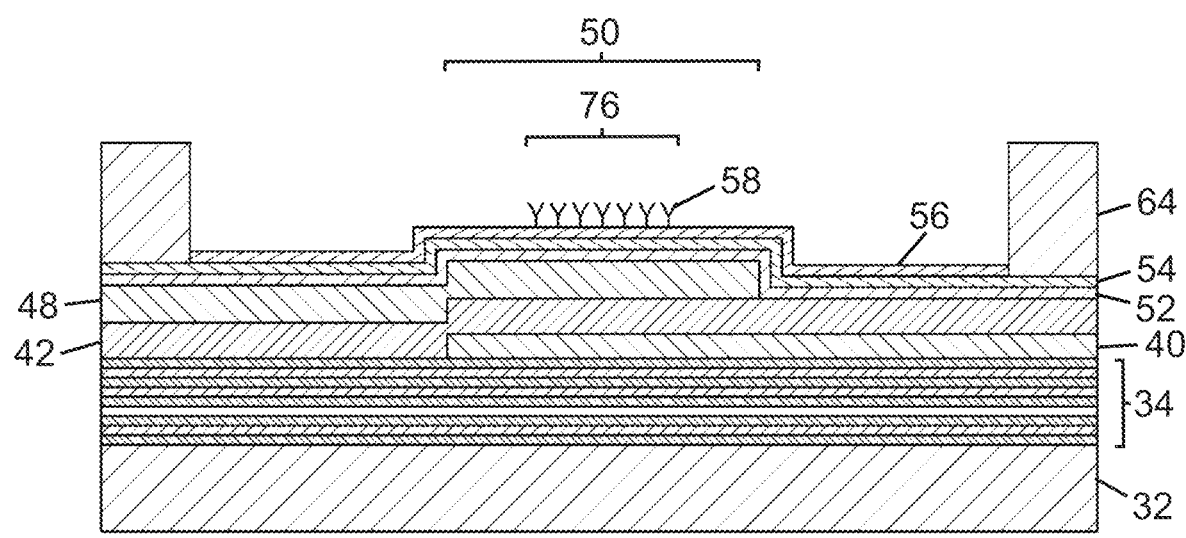

FIG. 5D illustrates the BAW resonator device portion of FIG. 5C following formation of a self-assembled monolayer (SAM) 56 over the interface layer 54 between the walls 64, and following application of functionalization material layer 58 over only a central portion 76 of the active region 50. Methods for applying functionalization material over only a central portion of an active region and over a SAM layer extending beyond the functionalization material are discussed hereinafter in connection with FIGS. 10 to 12A. Methods for applying functionalization material over only a central portion of an active region with one or more underlying layers (e.g., a SAM layer and an interface layer) also arranged over only a central portion of the active region are discussed herein after in connection with FIG. 6.

Figure 5E:
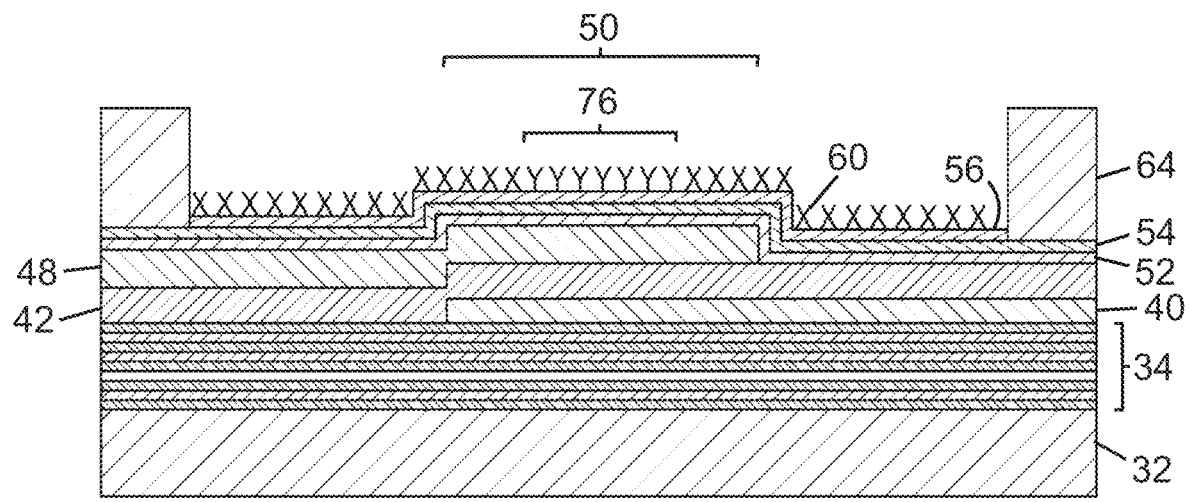
Figure 5F:
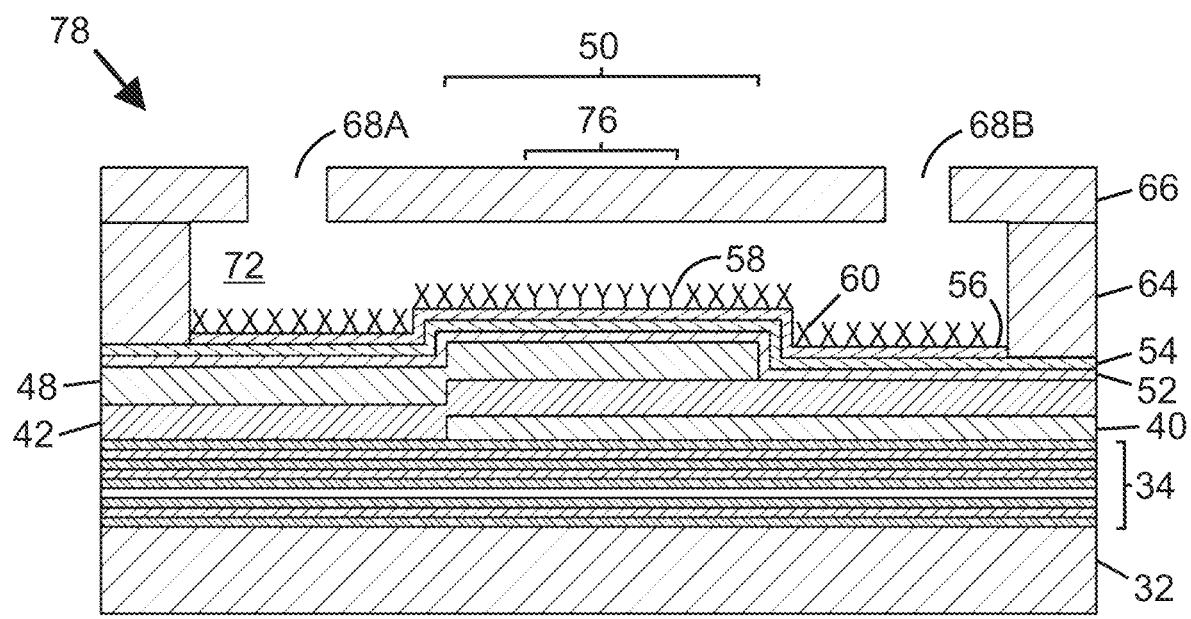
FIG. 5F is a schematic cross-sectional view of a portion of a fluidic device incorporating the intermediate structures illustrated in FIGS. 5A-5E, wherein less than an entirety of an active region of the BAW resonator structure is overlaid with functionalization material, according to one embodiment.

FIG. 5E illustrates the BAW resonator device portion of FIG. 5D following application of chemical or biological blocking material 60 over portions of the SAM 56 not previously overlaid with functionalization material layer 58. The chemical or biological blocking material 60 extends over peripheral portions of the active region 50 non-coincident with the central portion 76, and further extends over inactive regions between the active region 50 and the walls 64. FIG. 5F illustrates the device of FIG. 5E following addition of a cover or cap layer 66 arranged over top surfaces of the walls 64 to form a fluidic device 78. The cover or cap layer 66 defines fluidic ports 68A, 68B suitable to permit fluid (e.g., liquid) containing a target species to be introduced into a microfluidic passage 72 containing the active region 50 with functionalization material layer 58 arranged over a central portion 76 thereof.

Figure 5G:
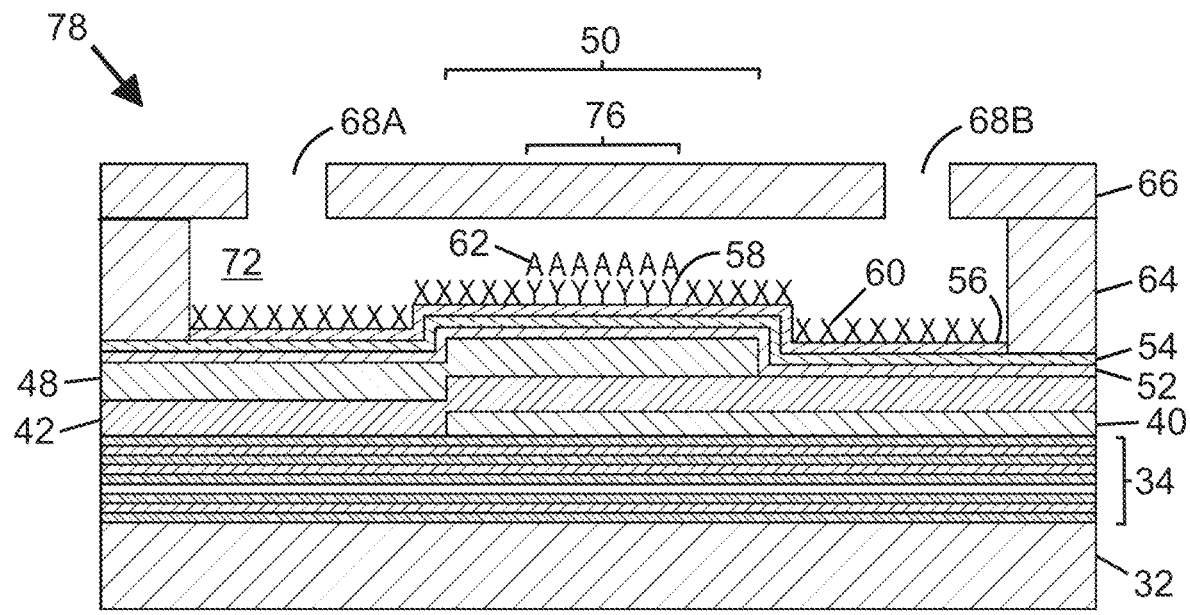
FIG. 5G is a schematic cross-sectional view of the fluidic device portion of FIG. 5F following use thereof, showing analyte bound to the functionalization material.

FIG. 5G illustrates the fluidic device 78 of FIG. 5F with an analyte 62 bound to the functionalization material layer 58, such as may occur after fluid containing the analyte 62 (or target species) is flowed (via one of the fluidic ports 68A, 68B) into the microfluidic passage 72 to contact the functionalization material layer 58. When a bulk acoustic wave is induced in the active region 50 by supplying an electrical (e.g., alternating current) signal to the bottom and top side electrodes 40, 48, a change in at least one of a frequency property, a magnitude property, or a phase property of the BAW resonator structure may be detected to indicate a presence and/or quantity of analyte 62 bound to the functionalization material layer 58. Since the functionalization material layer 58 is arranged over only a central portion 76 of the active region 50 exhibiting high sensitivity to changes in adsorbed mass, with peripheral portions of the active region 50 being devoid of adsorbed analyte, the fluidic device 78 is configured to provide a relatively large signal change responsive to binding of the analyte 62 to the functionalization material layer 58.

Figure 6:
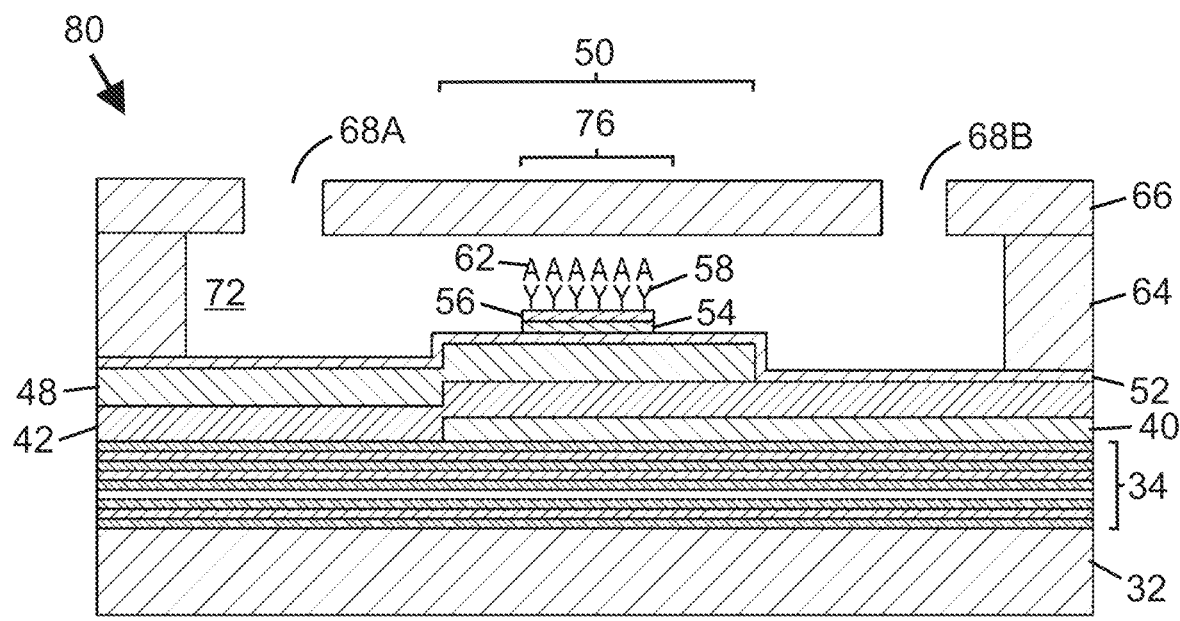
FIG. 6 is a schematic cross-sectional view of another fluidic device similar to the device of FIGS. 5F and 5G, with less than an entirety of an active region of the BAW resonator structure being overlaid with functionalization material, according to one embodiment.
Figure 7:
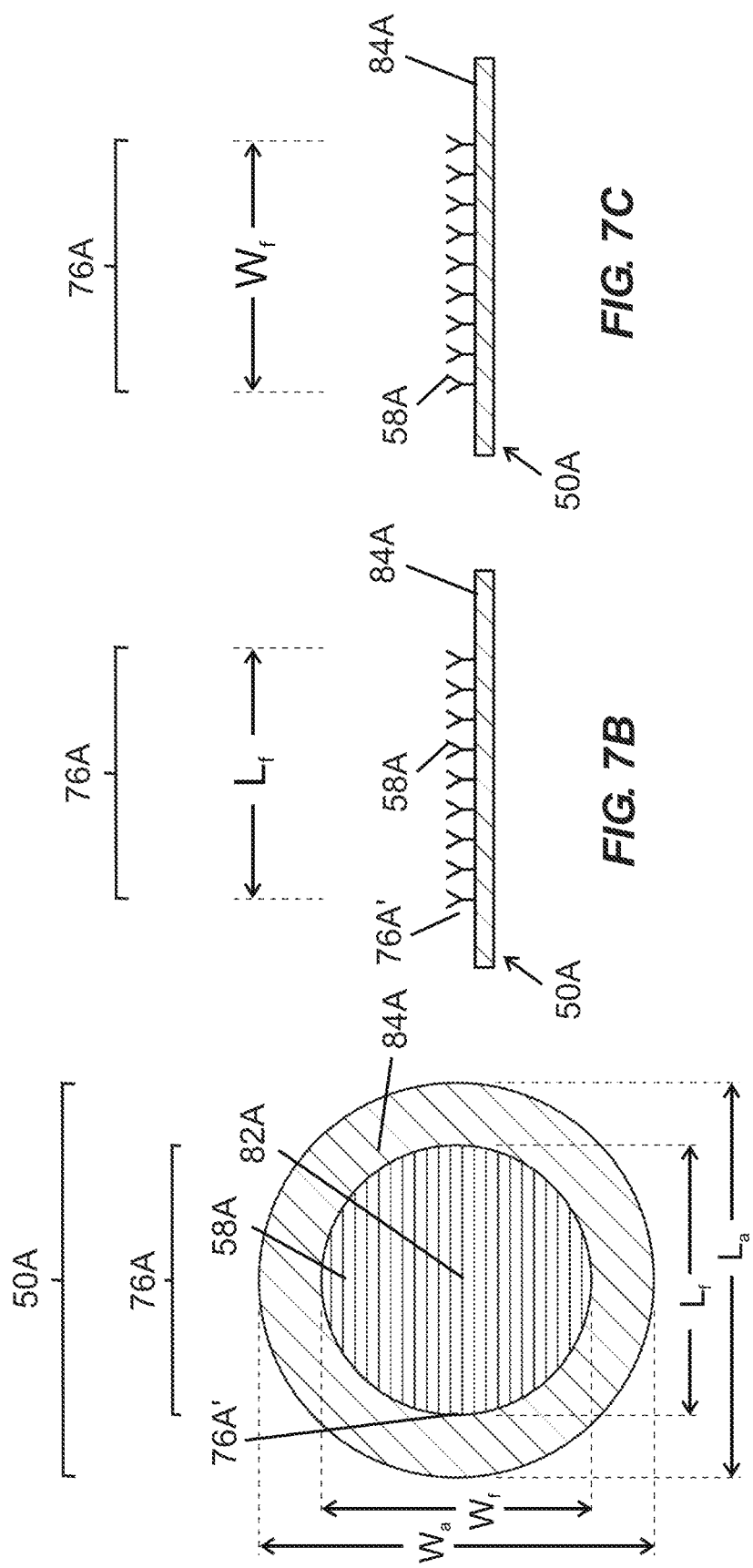
FIG. 7A is a schematic top plan view of an active region of a fluidic device incorporating a BAW resonator structure according to one embodiment, with a central portion of the active region overlaid with functionalization material arranged in a symmetric round configuration, and with an annular peripheral portion of the active region being devoid of functionalization material.
FIGS. 7B and 7C provide schematic cross-sectional side and front views, respectively, of the active region and functionalization material of FIG. 7A.
Figure 8:
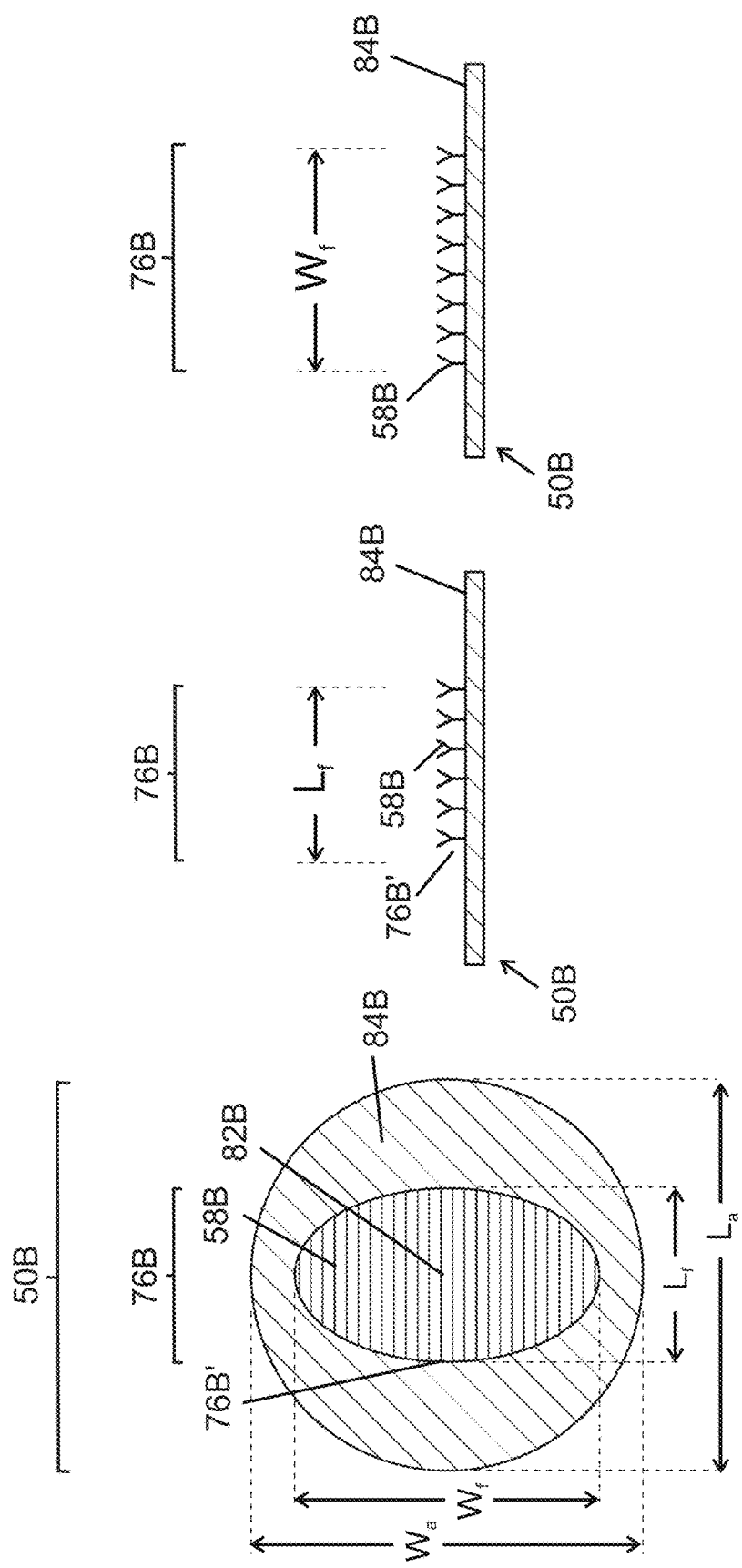
FIG. 8A is a schematic top plan view of an active region of a fluidic device incorporating a BAW resonator structure according to one embodiment, with a central portion of the active region overlaid with functionalization material arranged in an oval configuration having a greater width than length, with a maximum width of the active region being greater than that of the functionalization material, and with peripheral portions of the active region being devoid of functionalization material.
FIGS. 8B and 8C provide schematic cross-sectional side and front views, respectively, of the active region and functionalization material of FIG. 8A.
Figure 9:
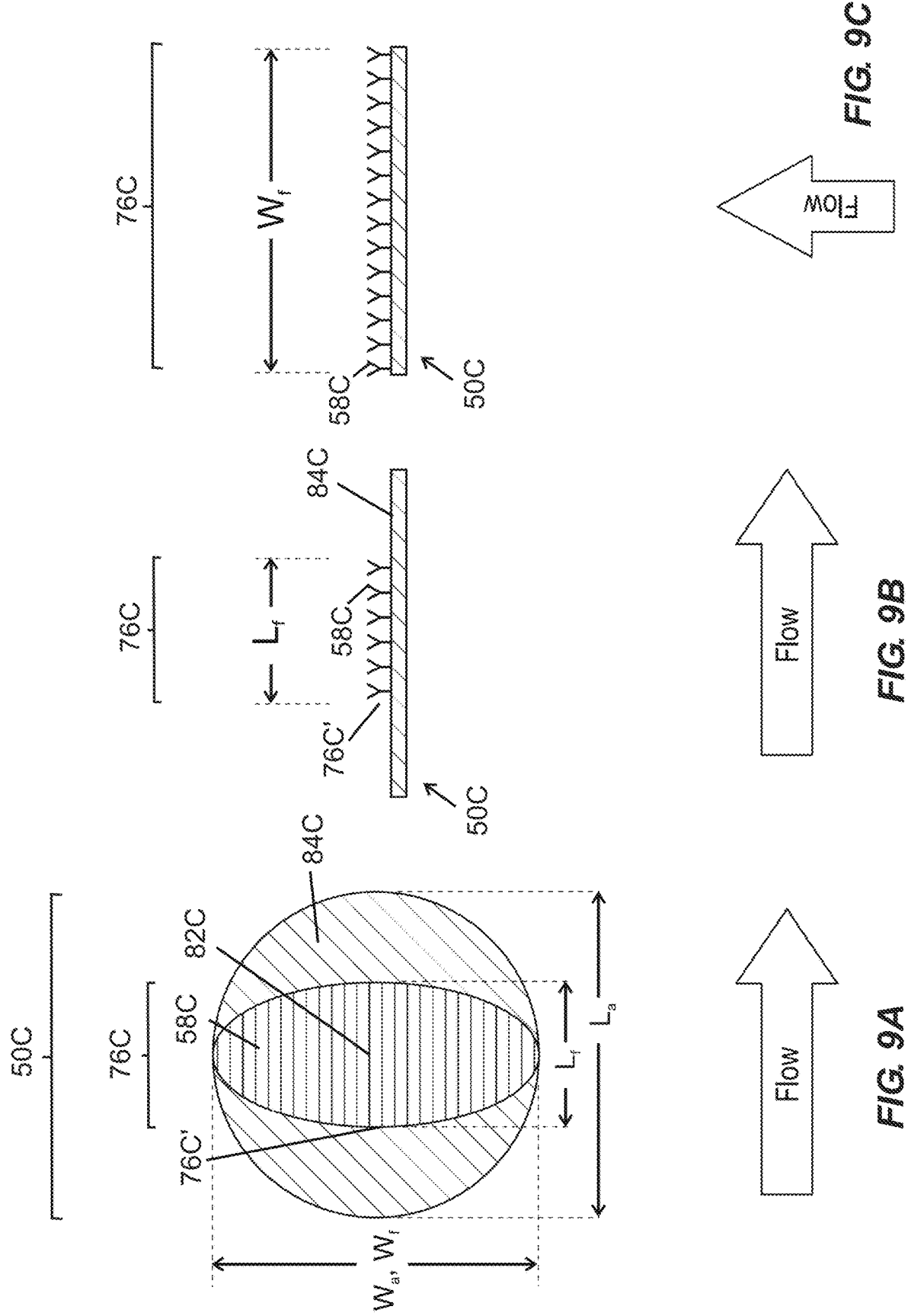
FIG. 9A is a schematic top plan view of an active region of a fluidic device incorporating a BAW resonator structure according to one embodiment, with a central portion of the active region overlaid with functionalization material arranged in an elongated oval configuration having a greater width than length, with a maximum width of the active region being equal to that of the functionalization material, and with crescent-shaped front and rear peripheral portions of the active region being devoid of functionalization material.
FIGS. 9B and 9C provide schematic cross-sectional side and front views, respectively of the active region and functionalization material of FIG. 9A.

FIG. 6 illustrates another fluidic device 80 similar to the fluidic device 78 illustrated in FIGS. 5F and 5G, wherein not only the functionalization material layer 58 but also the interface layer 54 and the SAM 56 are arranged over only a central portion 76 of the active region 50. The fluidic device 80 includes a substrate 32, an acoustic reflector 34, a piezoelectric material 42, bottom and top side electrodes 40, 48, and a hermeticity layer 52 over surfaces of the top side electrode 48 and the piezoelectric material 42. Walls 64 that are laterally displaced relative to the active region 50 extend upward from the hermeticity layer 52, and a cover or cap layer 66 defining fluidic ports 68A, 68B is arranged (e.g., adhered) to top surfaces of the walls 64 to enclose a microfluidic passage 72 containing the active region 50 overlaid with functionalization material layer 58. The interface layer 54 may be deposited by any suitable deposition technique disclosed herein (e.g., ALD, CVD, or PVD), preferably in conjunction with one or more masks (e.g., photolithographic and/or mechanical masks) to precisely control its placement over only a central portion 76 of the active region 50. The interface layer 54 preferably comprises a material including a hydroxylated oxide surface suitable for attachment of an organosilane-based SAM, or comprises gold or another noble metal suitable for attachment of a thiol-based SAM. After formation of the interface layer 54, the self-assembled monolayer (SAM) 56 may be deposited thereon, optionally in conjunction with one or more masks to control placement of the interface layer 54 solely over the SAM 56 registered with a central portion 76 of the active region 50. Optionally, one or more blocking materials (not shown) may be patterned over regions of the hermeticity layer 52 not overlaid with the interface layer 54 and the SAM 56. Following formation of the SAM 56, functionalization material 58 may be deposited on the SAM 56. Since functionalization material 58 tends to require a SAM 56 for adhesion, functionalization material 58 will tend to be deposited solely on the SAM 56 over the central portion 76 of the active region 50. If desired, optionally using one or more photolithographic or mechanical masks may further be used during application of functionalization material 58.

FIGS. 7A to 9C illustrate active regions of fluidic devices incorporating BAW resonator structures, with central portions of active regions being overlaid with functionalization material in three different configurations, and with FIGS. 8A to 9C further including hollow arrows indicating a direction of fluid flow relative to the respective active region. Although three specific configurations are shown (i.e., a first, second, and third configuration in FIGS. 7A-7C, FIGS. 8A-8C, and FIGS. 9A-9C, respectively), it is to be appreciated that functionalization material may be provided over a central portion of an active region in any suitable shape or configuration within the scope of the appended claims. Additionally, although active regions having round shapes are illustrated for ease of disclosure, it is to be appreciated that an active region of a resonator structure is not so limited, and that an active region may include any suitable rectangular, trapezoidal, oval, curved, or other geometric shape.

FIG. 7A is a schematic top plan view of an active region 50A of a fluidic device incorporating a BAW resonator structure according to one embodiment, with a central portion 76A of the active region 50A (being round in shape) overlaid with functionalization material 58A arranged in a symmetric round configuration, and with an annular peripheral portion 84A of the active region 50A being devoid of functionalization material. The active region 50A includes a maximum width $W_a$ and a maximum length $L_a$, and the functionalization material includes a maximum width $W_f$ and a maximum length $L_f$. The active region 50A includes a center point 82A having maximum sensitivity, with the center point 82A coinciding with a center of the central portion 76A that is overlaid with functionalization material 58A. The functionalization material 58A is arranged in a shape comprising a curved leading edge, wherein a center point 76A' of the curved leading edge is arranged between the center point 82A of the active region 50A and an inlet port (not shown) of a fluidic device containing the active region 50A. Although the central portion 76A is symmetric and is concentric with the active region 50A, in alternative embodiments a central portion overlaid with functionalization material may be non-symmetric and/or non-concentric with respect to an associated active region. Additionally, although the leading edge of the functionalization material 58A is arranged in a curved shape, it is to be appreciated that the leading edge may be fashioned in any suitable shape, such as straight, angled, sawtooth, or another geometric configuration. FIGS. 7B and 7C provide schematic cross-sectional side and front views, respectively, of the functionalization material 58A and active region 50A of FIG. 7A, with the functionalization material 58A arranged over the central portion 76A of the active region 50A, and with the central portion 76A being surrounded with the peripheral portion 84A that is devoid of functionalization material.

FIG. 8A is a schematic top plan view of an active region 50B of a fluidic device incorporating a BAW resonator structure according to one embodiment, with a central portion 76B of the active region 50B (being round in shape) overlaid with functionalization material 58B arranged in an oval configuration having a greater width than length, with a maximum width of the active region being greater than that of the functionalization material 58B, and with peripheral portions of the active region being devoid of functionalization material. The active region 50B includes a maximum width $W_a$ and a maximum length $L_a$, and the functionalization material 58B includes a maximum width $W_f$ and a maximum length $L_f$. As illustrated, $W_f > L_f$, $W_a > W_f$, and $L_a > L_f$. The active region 50B includes a center point 82B having maximum sensitivity, with the center point 82B coinciding with a center of the central portion 76B that is overlaid with functionalization material 58B. FIGS. 8B and 8C provide schematic cross-sectional side and front views, respectively, of the active region 50B and functionalization material 58B of FIG. 8A, with the functionalization material 58B arranged over the central portion 76B of the active region 50B, and with the central portion 76B being surrounded with the peripheral portion 84B that is devoid of functionalization material. The functionalization material 58B is arranged in a shape comprising a curved leading edge, wherein a center point 76B' of the curved leading edge is arranged between the center point 82B of the active region 50B and an inlet port (not shown) of a fluidic device containing the active region 50B.

FIG. 9A is a schematic top plan view of an active region 50C of a fluidic device incorporating a BAW resonator structure according to one embodiment, with a central portion 76C of the active region 50C overlaid with functionalization material 58C arranged in an elongated oval configuration having a greater width than length, with a maximum width of the active region 50C being equal to a maximum width of the functionalization material 58C, and with crescent-shaped front and rear peripheral portions 84C of the active region 50C being devoid of functionalization material. The active region 50C includes a maximum width $W_a$ and a maximum length $L_a$, and the functionalization material 58C includes a maximum width $W_f$ and a maximum length $L_f$. As illustrated, $W_f > L_f$, $W_a = W_f$, and $L_a > L_f$. The active region 50C includes a center point 82C having maximum sensitivity, with the center point 82C coinciding with a center of the central portion 76C that is overlaid with functionalization material 58C. FIGS. 9B and 9C provide schematic cross-sectional side and front views, respectively, of the active region 50C and functionalization material 58C of FIG. 9A, with the functionalization material 58C arranged over the central portion 76C of the active region 50C, and with the central portion 76C being bounded at front and rear with the crescent-shaped front and rear peripheral portions 84C that are devoid of functionalization material. The functionalization material 58C is arranged in a shape comprising a curved leading edge, wherein a center point 76C' of the curved leading edge is arranged between the center point 82C of the active region 50C and an inlet port (not shown) of a fluidic device containing the active region 50C.

Comparing the configurations shown in FIGS. 7A, 8A, and 9A, the round configuration of the central portion 76A bearing functionalization material 58A in FIG. 7A is likely to exhibit greater sensitivity than if the entirety of the active region 50A were overlaid with functionalization material 58A, but the sensitivity may not be optimal for a very low analyte concentration since a leading edge of the functionalization material 58A (at the boundary between the peripheral portion 84A and the central portion 76A) is significantly closer to a lateral edge of the active region 50A than the center point 82A. Additionally, the absence of functionalization material along a subset of the peripheral portion 84A means that some analyte may travel immediately over the peripheral portion 84A without interacting with any functionalization material 58A. The oval configuration of the central portion 76B bearing functionalization material 58B in FIG. 8A likely entails enhanced sensitivity over the configuration shown in FIG. 7A, since a leading edge of the functionalization material 58B (at the boundary between the peripheral portion 84B and the central portion 76B) is closer to the center point 82B than to a lateral edge of the active region 50B, such that any initial analyte accumulation on a leading edge of the functionalization material 58B will occur closer to the center point 82B than was the case in FIG. 7A. However, the absence of functionalization material along a subset of the peripheral portion 84B means that some analyte may travel immediately over the peripheral portion 84B (i.e., at the narrowest portions thereof) without interacting with (i.e., binding to) any functionalization material 58B. The elongated oval configuration of the central portion 76C bearing functionalization material 58C in FIG. 9A likely entails even higher sensitivity than the configuration of FIG. 8A. since the presence of functionalization material 58C across the entire width $W_a$ of the active region means that any analyte traveling immediately over the active region 50C is likely to interact with (i.e., bind to) some functionalization material 58C.

Figure 10:
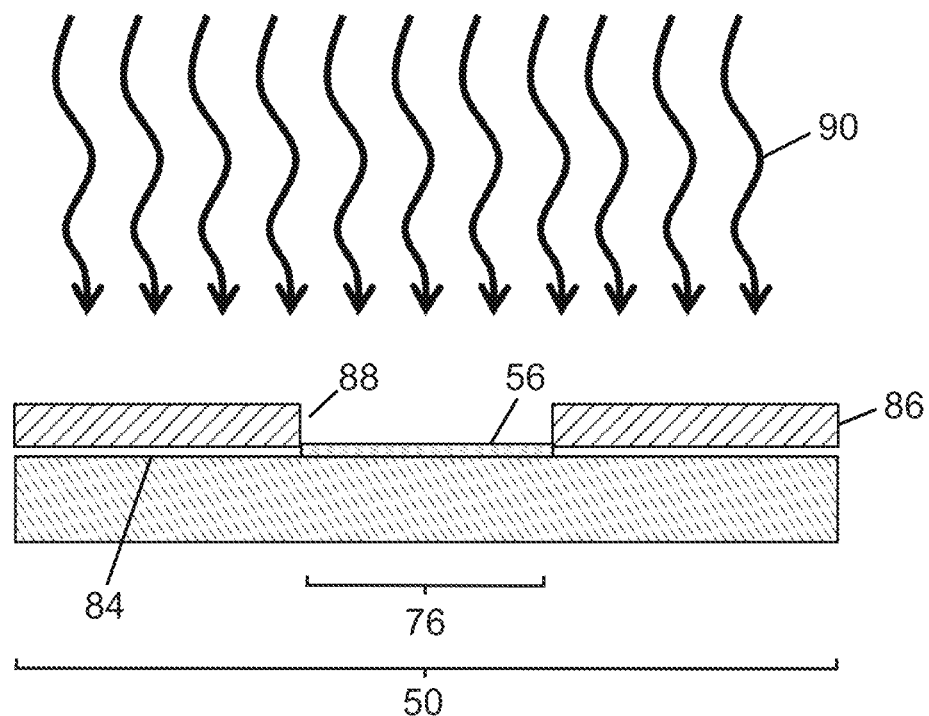
FIG. 10 is a schematic side cross-sectional view of an active region of a BAW resonator structure over which a window-defining mechanical mask is arranged, to permit precursor material for a self-assembled monolayer to be deposited through a window over a portion of the active region.
Figure 11:
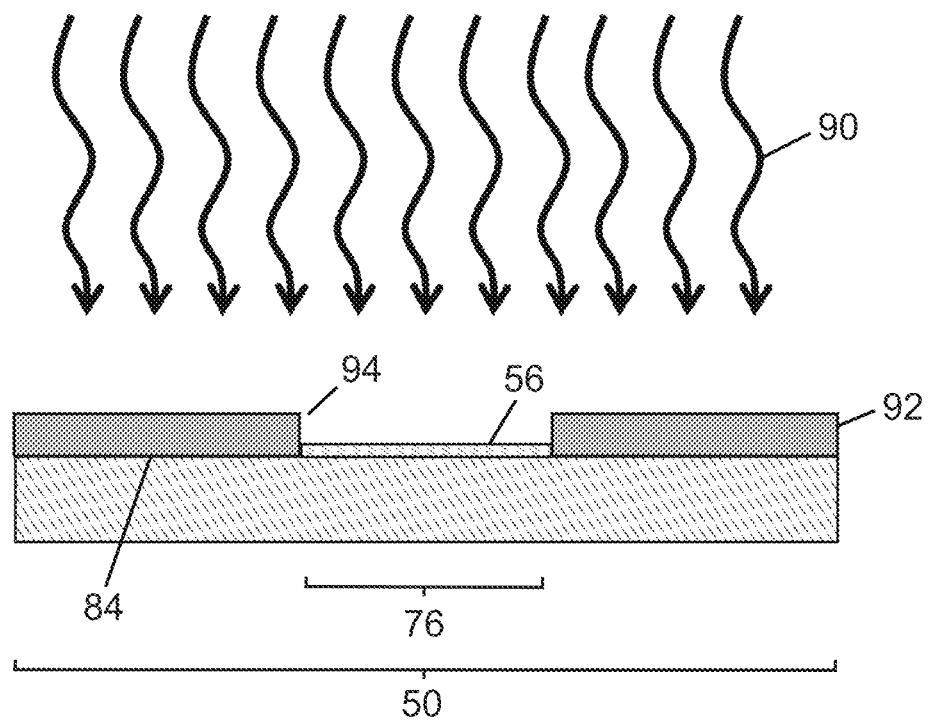
FIG. 11 is a schematic side cross-sectional view of an active region of a BAW resonator structure overlaid with a patterned photoresist layer, to permit precursor material for a self-assembled monolayer to be deposited through a window in the photoresist layer over a portion of the active region.

FIGS. 10-12 illustrate methods for controlling localized deposition of a self-assembled monolayer (SAM) to enable placement of a SAM over less than an entirety of an active region of a resonator, and thereby enable functionalization material overlying the SAM to be similarly placed over less than an entirety of an active region.

FIG. 10 is a schematic side cross-sectional view of an active region 50 of a BAW resonator structure over which a mechanical mask 86 defining a window 88 is arranged, to permit precursor material 90 for a self-assembled monolayer 56 to be deposited through the window 88 over a central portion 76 of the active region 50 without formation of a SAM over peripheral portions 84 of the active region 50. Following formation of the SAM 56, the mechanical mask 86 may be removed. One or more windows 88 may be formed in the mechanical mask 86 by any suitable means such as etching, laser cutting, waterjet cutting, or the like.

FIG. 11 is a schematic side cross-sectional view of an active region 50 of a BAW resonator structure overlaid with a patterned photoresist layer 92, to permit precursor material 90 for a SAM 56 to be deposited through a window 94 in the photoresist layer 92 over a central portion 76 of the active region 50 without formation of a SAM over peripheral portions 84 of the active region 50. The window 94 in the photoresist layer 92 may be formed by photolithographic etching or other conventional means. Following formation of the SAM 56, the photoresist layer 92 may be removed, preferably by chemical means not tending to degrade the SAM 56. In certain embodiments, one or more removable protective layers (e.g., an inverse mechanical mask or chemical coating) may be arranged over the SAM 56 during removal of the photoresist layer 92 to prevent degradation of the SAM 56, followed by removal of the protective layer(s).

Figure 12A:
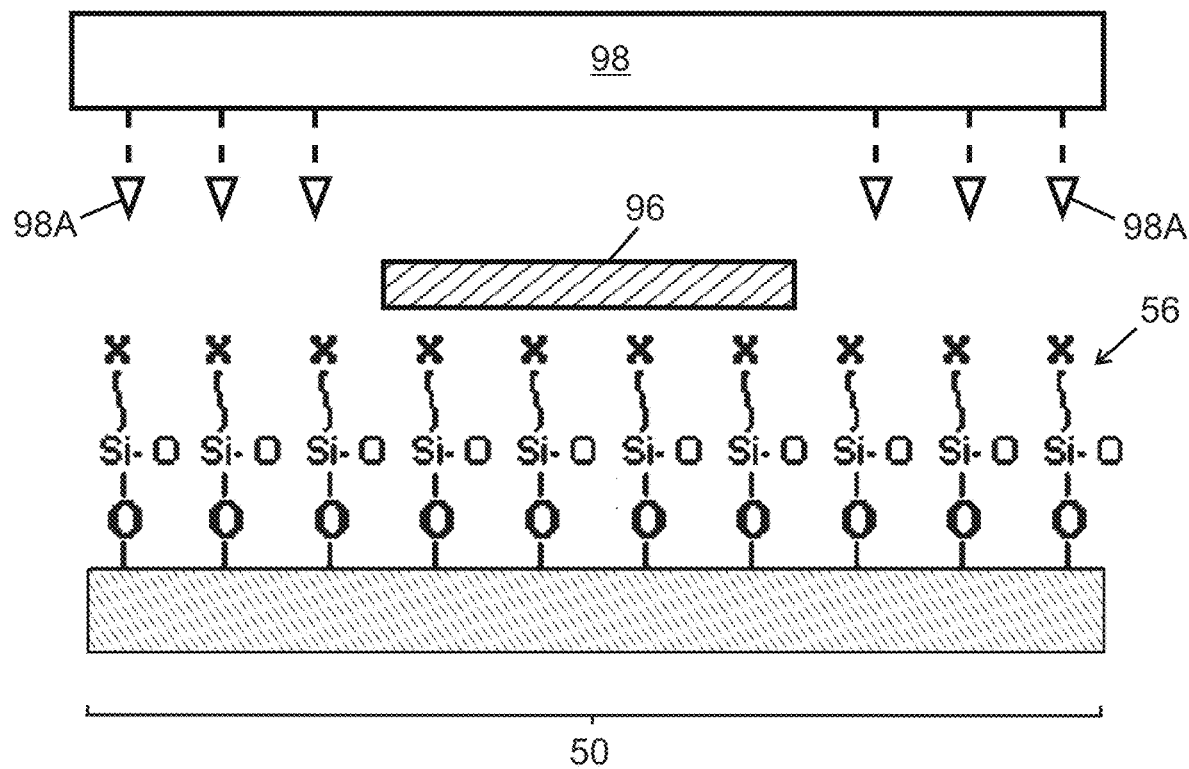
FIG. 12A is a schematic side cross-sectional view of an active region of a BAW resonator structure overlaid with an organosilane-based self-assembled monolayer (SAM), with a radiation-blocking mechanical mask arranged over the SAM, and with an electromagnetic radiation source positioned to transmit light past openings in the mask for selective removal of portions of the SAM.
Figure 12B:
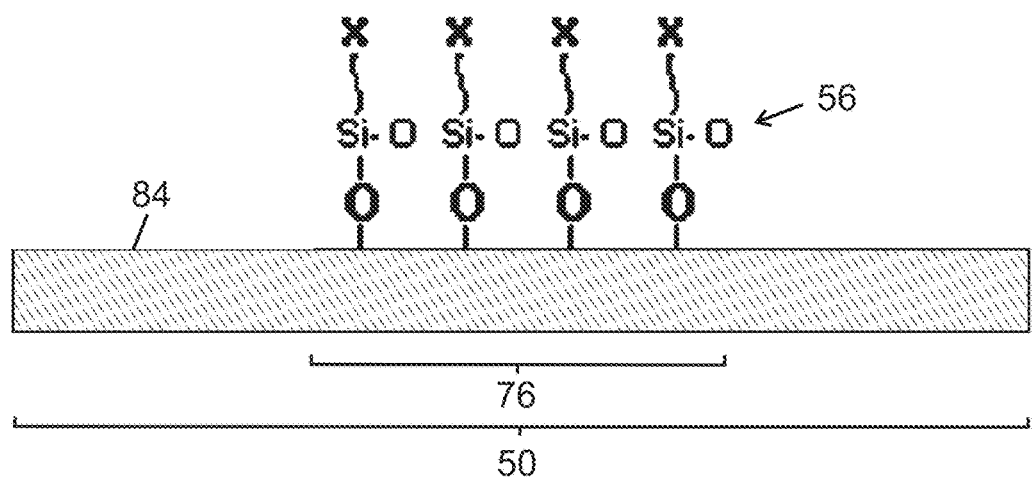
FIG. 12B is a schematic side cross-sectional view of the active region of the BAW resonator structure of FIG. 12A following removal of the SAM along peripheral portions of the active region.

FIG. 12A is a schematic side cross-sectional view of an active region 50 of a BAW resonator structure overlaid with an organosilane-based SAM 56, with a radiation-blocking mechanical mask 96 arranged over the SAM 56, and with an electromagnetic radiation source 98 positioned to transmit light beams 98A past apertures (openings) or boundaries of the mechanical mask 96 for selective removal of portions of the SAM 56. In certain embodiments, the electromagnetic radiation source 98 is configured to emit electromagnetic radiation in the ultraviolet range comprising a peak wavelength in a range of from about 150 nm to 400 nm. FIG. 12B is a schematic side cross-sectional view of the active region 50 of the BAW resonator structure of FIG. 12A following removal of the SAM 56 along peripheral portions 84 of the active region 50 to cause only a central portion 76 of the active region 50 to be overlaid with the SAM 56. In certain embodiments, a second mechanical mask (not shown) may be applied over the SAM 56 overlying the central portion 76 of the active region 50 with apertures arranged over the peripheral portions 84, and blocking layer material (not shown) may be applied through at least one aperture defined in the second mechanical mask to cover portions of the BAW resonator structure not covered with the SAM 56 (e.g., including by not limited to the peripheral portions 84 of the active region 50).

Figure 13:
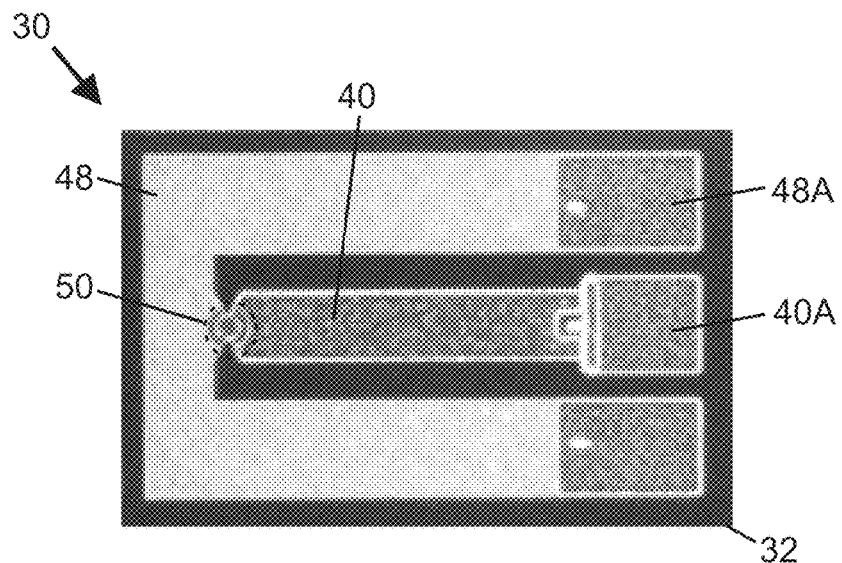
FIG. 13 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 13 is a top plan view photograph of a bulk acoustic wave MEMS resonator device 30 (consistent with the portion of a resonator device 30 illustrated in FIG. 2) suitable for receiving a hermeticity layer, an interface layer, a self-assembled monolayer, and functionalization (e.g., specific binding) material as disclosed herein. The MEMS resonator device 30 includes a piezoelectric material (not shown) arranged over a substrate 32, a bottom side electrode 40 arranged under a portion of the piezoelectric material, and a top side electrode 48 arranged over a portion of the piezoelectric material, including an active region 50 in which the piezoelectric material is arranged between overlapping portions of the top side electrode 48 and the bottom side electrode 40. Externally accessible contacts 40A, 48A are in electrical communication with the bottom side electrode 40 and the top side electrode 48, respectively. After portions of the MEMS resonator device 30 are overlaid with an interface layer, a self-assembled monolayer, and functionalization (e.g., specific binding) material as disclosed herein, the resonator device 30 may be used as a sensor and/or incorporated into a microfluidic device. If desired, multiple MEMS resonator devices 30 may be provided in an array on a single substrate 32.

Figure 14:
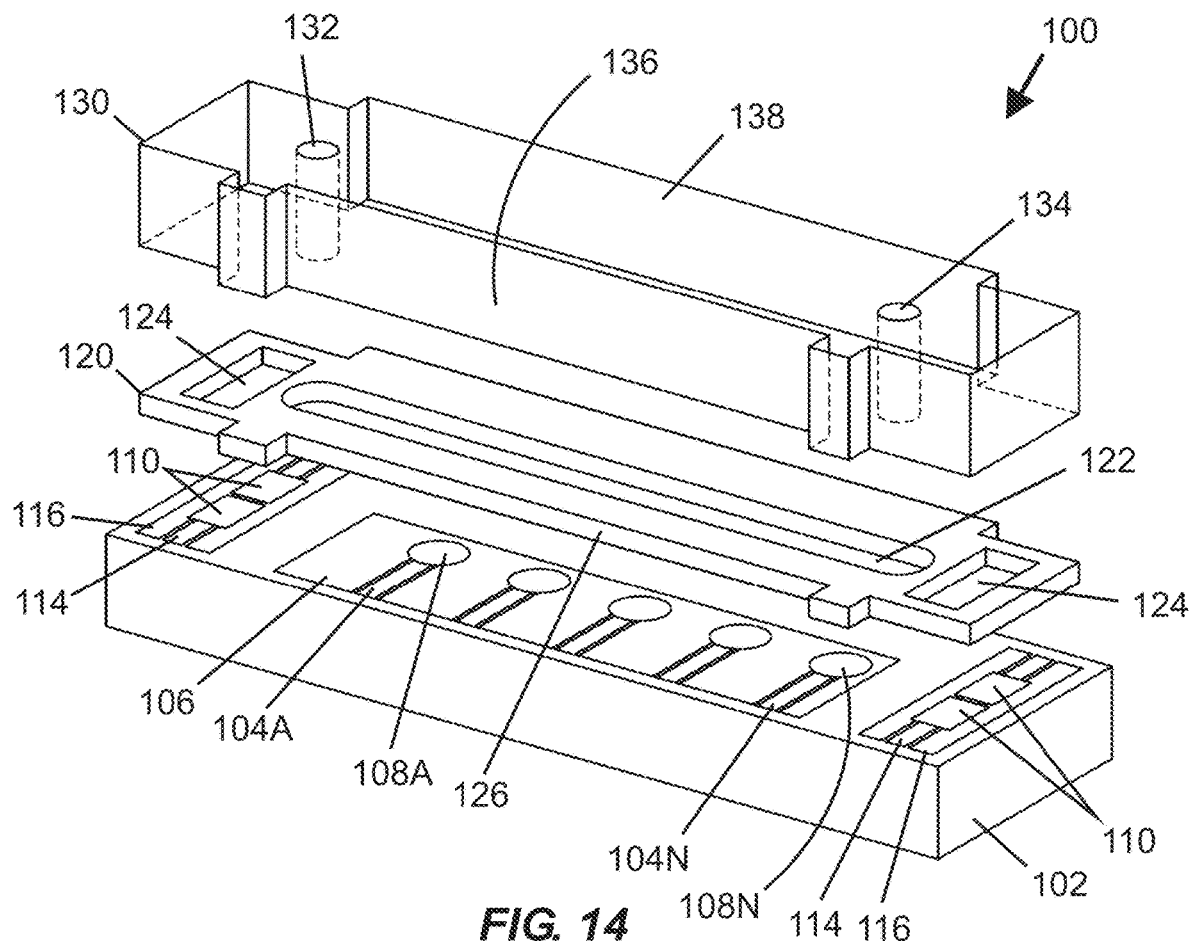
FIG. 14 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer.

FIG. 14 is a perspective assembly view of a microfluidic device 100 incorporating a substrate 102 with multiple bulk acoustic wave MEMS resonator devices, an intermediate layer 120 defining a central microfluidic channel 122 registered with active regions 108A-108N of the MEMS resonator devices, and a cap or cover layer 130 arranged to cover the intermediate layer 120. Top central portions of the substrate 102, which includes an acoustic reflector (not shown) and a piezoelectric material (not shown), include a top side electrode 106 and bottom side electrodes 104A-104N. Regions in which the foregoing electrodes overlap one another with the piezoelectric material arranged therebetween embody active regions 108A-108N. Any suitable number of active regions 108A-108N may be provided and fluidically arranged in series or parallel, although five active regions are illustrated in FIG. 14. Top peripheral (or top end) portions of the substrate 102 further include reference top side electrodes 116 and reference bottom side electrodes 114 in communication with reference overlap regions 110. Such reference overlap regions 110 are not exposed to fluid, and are present to provide a basis for comparing signals obtained from the active regions 108A-108N exposed to fluid within the central microfluidic channel 122. The substrate 102 is overlaid with the intermediate (e.g., wall-defining) layer 120, wherein the central microfluidic channel 122 is intended to receive fluid, and defines peripheral chambers 124 arranged to overlie the reference overlap regions 110 in a sealed fashion. The intermediate layer 120 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 120 further includes a lateral inset region 126 that enables lateral portions of the top side electrode 106 and bottom side electrodes 104A-104N to be accessed upon assembly of the microfluidic device 100. The cap or cover layer 130 includes a lateral inset region 136 registered with the lateral inset region 126 of the intermediate layer 120, and includes microfluidic ports 132, 134 accessible along a top surface 138 and registered with end portions of the central microfluidic channel 122 defined in the intermediate layer 120 to permit fluid (e.g., liquid) to be supplied to the central microfluidic channel 122 over the active regions 108A-108N. Preferably, at least the electrodes 104A-104N, 106 are overlaid with a hermeticity layer, an interface layer, a self-assembled monolayer, and functionalization (e.g., specific binding) material as disclosed herein. Microfluidic devices according to other configurations may be provided, as will be recognized by those skilled in the art upon review of the present disclosure.

FIG. 15 is a schematic cross-sectional view of a film bulk acoustic wave resonator (FBAR) structure 140 including an active region 50, including at least portions thereof being subject to being overlaid with an interface layer and a self-assembled monolayer (SAM) suitable for receiving a functionalization material (e.g., specific binding or non-specific binding material), according to one embodiment. The FBAR structure 140 includes a substrate 142 (e.g., silicon or another semiconductor material) defining a cavity 144 that is covered by a support layer 146 (e.g., silicon dioxide). A bottom side electrode 40 is arranged over a portion of the support layer 146, a piezoelectric material 42 preferably embodying inclined c-axis hexagonal crystal structure piezoelectric material (e.g., AlN or ZnO) is arranged over the bottom side electrode 40 and the support layer 146, and a top side electrode 48 is arranged over at least a portion of a top surface of the piezoelectric material 42. A portion of the piezoelectric material 42 arranged between the top side electrode 48 and the bottom side electrode 40 embodies an active region 50 of the FBAR structure 140. The active region 50 is arranged over and registered with the cavity 144 disposed below the support layer 146. The cavity 144 serves to confine acoustic waves induced in the active region 50 by preventing dissipation of acoustic energy into the substrate 142, since acoustic waves do not efficiently propagate across the cavity 144. In this respect, the cavity 144 provides an alternative to the acoustic reflector 34 illustrated in FIGS. 2 and 4-6. Although the cavity 144 shown in FIG. 15 is bounded from below by a thinned portion of the substrate 142, in alternative embodiments at least a portion of the cavity 144 may extend through an entire thickness of the substrate 142. Steps for forming the FBAR structure 140 may include defining the cavity 144 in the substrate 142, filling the cavity 144 with a sacrificial material (not shown) optionally followed by planarization of the sacrificial material, depositing the support layer 146 over the substrate 142 and the sacrificial material, removing the sacrificial material (e.g., by flowing an etchant through vertical openings defined in the substrate 142 or the support layer 146, or lateral edges of the substrate 142), depositing the bottom side electrode 40 over the support layer 146, growing (e.g., via sputtering or other appropriate methods) the piezoelectric material 42, and depositing the top side electrode 48.

FIG. 16 is a schematic cross-sectional view of a FBAR structure 140 according to FIG. 15, following addition of a hermeticity layer 52, an interface layer 54, a self-assembled monolayer 56, and a functionalization material layer 58 (e.g., specific binding material) over at least portions of the FBAR structure 140. The functionalization material layer 58 is arranged solely over a central portion 76 of the active region 50, with the interface layer 54 and the SAM 56 being similarly arranged solely over the central portion 76. As shown in FIG. 16, analyte 62 is bound to the functionalization material layer 58, such as may occur following exposure of the functionalization material layer 58 to a medium (e.g., liquid or other fluid) containing the analyte, optionally as part of a microfluidic device.

Those skilled in the art will recognize improvements and modifications to the preferred embodiments of the present disclosure. All such improvements and modifications are considered within the scope of the concepts disclosed herein and the claims that follow.

What is claimed is:

1. A micro-electrical-mechanical system (MEMS) resonator device comprising:
   a substrate;
   a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region, the top side electrode comprises an active area portion that overlaps the bottom side electrode and is coincident with the active region, the active area portion includes an active area width, and the active area portion includes an active area length extending perpendicular to the active area width; and
   at least one functionalization material arranged over at least a central portion of the top side electrode, wherein the at least one functionalization material extends a maximum length in a range of from about 40% to about 90% of the active area length and extends a maximum width in a range of from about 70% to 95% of the active area width.

2. The MEMS resonator device of claim 1, wherein the maximum width of the at least one functionalization material exceeds the maximum length thereof.

3. The MEMS resonator device of claim 1, further comprising a self-assembled monolayer arranged between the top side electrode and the at least one functionalization material.

4. The MEMS resonator device of claim 1, further comprising an interface layer arranged between the top side electrode and the at least one functionalization material.

5. The MEMS resonator device of claim 4, wherein the top side electrode comprises a non-noble metal, and the MEMS resonator device further comprises a hermeticity layer arranged between the interface layer and the top side electrode.

6. The MEMS resonator device of claim 4, further comprising a self-assembled monolayer arranged between the interface layer and the at least one functionalization material.

7. The MEMS resonator device of claim 1, wherein the at least one functionalization material comprises a specific binding material or a non-specific binding material.

8. The MEMS resonator device of claim 1, wherein the piezoelectric material comprises a c-axis having an orientation distribution that is predominantly non-parallel to normal of a face of the substrate.

9. The MEMS resonator device of claim 1, further comprising at least one acoustic reflector element arranged between the substrate and the bulk acoustic wave resonator structure.

10. The MEMS resonator device of claim 1, wherein the substrate defines a recess, and the MEMS resonator device further comprises a support layer arranged between the bulk acoustic wave resonator structure and the recess, wherein the active region is arranged over at least a portion of the support layer and at least a portion of the recess.

11. The MEMS resonator device of claim 1, further comprising a blocking layer arranged over a portion of the piezoelectric material non-coincident with the active region.

12. A sensor comprising the MEMS resonator device of claim 1.

13. A fluidic device comprising the MEMS resonator device of claim 1, and a fluidic passage containing the active region and arranged to conduct a flow of liquid to contact the at least one functionalization material, wherein the fluidic passage is arranged to conduct the flow of liquid from an inlet port upstream of the active region toward the active region in a direction that is substantially parallel to the active area length.

14. The fluidic device of claim 13, wherein the at least one functionalization material is arranged in a shape comprising a leading edge, wherein a center point of the leading edge is arranged between the inlet port and a center point of the active region.

15. A method for biological or chemical sensing, the method comprising:
supplying a fluid containing a target species into the fluidic passage of the fluidic device according to claim 13, wherein said supplying is configured to cause at least some of the target species to bind to the at least one functionalization material;
inducing a bulk acoustic wave in the active region; and
sensing a change in at least one of a frequency property, a magnitude property, or a phase property of the bulk acoustic wave resonator structure to indicate at least one of presence or quantity of target species bound to the at least one functionalization material.

16. A method for fabricating a micro-electrical-mechanical system (MEMS) resonator device, the method comprising:
forming a bulk acoustic wave resonator structure including a piezoelectric material, a top side electrode arranged over a portion of the piezoelectric material, and a bottom side electrode arranged between the piezoelectric material and a substrate, wherein a portion of the piezoelectric material is arranged between the top side electrode and the bottom side electrode to form an active region, the top side electrode comprises an active area portion that overlaps the bottom side electrode and is coincident with the active region, the active area portion includes an active area width, and the active area portion includes an active area length extending perpendicular to the active area width; and
depositing at least one functionalization material arranged over at least a central portion of the top side electrode, wherein the at least one functionalization material extends a maximum length in a range of from about 40% to about 90% of the active area length and extends a maximum width in a range of from about 70% to 95% of the active area width.

17. The method of claim 16, further comprising forming a self-assembled monolayer over at least a portion of the top side electrode prior to said depositing of the at least one functionalization material, wherein the at least one functionalization material is arranged over at least a portion of the self-assembled monolayer.

18. The method of claim 17, wherein the forming of a self-assembled monolayer over at least a portion of the top side electrode comprises:
applying the self-assembled monolayer over the top side electrode;
arranging a first mechanical mask over the self-assembled monolayer, wherein the first mechanical mask defines at least one first aperture through which at least one first portion of the self-assembled monolayer is exposed; and
transmitting electromagnetic radiation comprising a peak wavelength in a range of from about 150 nm to 400 nm through the at least one first aperture to interact with the at least one first portion of the self-assembled monolayer to promote removal of the at least one first portion of the self-assembled monolayer.

19. The method of claim 18, further comprising:
arranging a second mechanical mask over at least a portion of the bulk acoustic wave resonator structure including the active region, wherein the second mechanical mask defines at least one second aperture through which at least one second portion of the self-assembled monolayer is exposed; and
applying a blocking layer through the at least one second aperture to the at least one second portion of the self-assembled monolayer.

20. The method of claim 16, further comprising forming at least one wall over a portion of the bulk acoustic wave resonator structure and defining a fluidic passage overlying the active region, wherein the fluidic passage is arranged to conduct a flow of liquid from an inlet port upstream of the active region toward the active region in a direction that is substantially parallel to the active area length, and the fluidic passage is arranged to conduct the flow of liquid to contact the at least one functionalization material.

21. The method of claim 16, wherein the at least one functionalization material extends a maximum length in a range of from about 50% to about 90% of the active area length and extends a maximum width in a range of from about 70% to 95% of the active area width.

* * * * *